United States Patent
Mueller et al.

(10) Patent No.: US 10,190,136 B2
(45) Date of Patent: Jan. 29, 2019

(54) MOUSE MODEL OF ALPHA-ONE ANTITRYPSIN (AAT) DEFICIENCY

(71) Applicant: University of Massachusetts, Boston, MA (US)

(72) Inventors: Christian Mueller, Worcester, MA (US); Florie Borel, Saint Martin (FR)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/595,554

(22) Filed: May 15, 2017

(65) Prior Publication Data

US 2017/0327843 A1     Nov. 16, 2017

Related U.S. Application Data

(60) Provisional application No. 62/336,220, filed on May 13, 2016.

(51) Int. Cl.
| | |
|---|---|
| *A01K 67/027* | (2006.01) |
| *C12N 15/85* | (2006.01) |
| *C07K 14/81* | (2006.01) |
| *C12N 15/09* | (2006.01) |
| *C12N 15/00* | (2006.01) |

(52) U.S. Cl.
CPC ...... *C12N 15/8509* (2013.01); *C07K 14/8125* (2013.01); *C12N 15/09* (2013.01); *C12N 15/00* (2013.01); *C12N 2015/8527* (2013.01)

(58) Field of Classification Search
USPC .................................................. 800/3, 8–20
See application file for complete search history.

(56) References Cited

PUBLICATIONS

Gosai, PLoS, 2010, vol. 5, No. 11, e15460.*
Heit (Human Genomics, 2013, vol. 7, No. 1, p. 22).*
Wang (Exp. Lung Res., 2011, vol. 37, p. 291-300).*
Wang (Cell, 2013, vol. 153, p. 910-918).*
Bae et al., "Cas-OFFinder: a fast and versatile algorithm that searches for potential off-target sites of Cas9 RNA-guided endonucleases," Bioinformatics, 2014, 30: 1473-1475.
Barbour et al., "The murine alpha(1)-proteinase inhibitor gene family: polymorphism, chromosomal location, and structure," Genomics, Nov. 2002, 80: 515-522.
Borel et al., "167. Genome Editing to Generate the First Mouse Model of Alpha-One Antitrypsin Deficiency, the Leading Cause of Genetic COPD," Molecular Therapy, May 2016, 24: S65, 1 page (Abstract Only).
Borel et al., "Genome editing to generate the first mouse model of alpha-one antitrypsin deficiency, the leading cause of genetic COPD," Poster, Presented at the Gene Therapy Center, University of Massachusetts Medical School, Worcester, MA, Tufts University, Grafton, MA; Molecular Therapy, May 2016, 24(Supp.1): S65, 1 page.

Buist et al., "International variation in the prevalence of COPD (the BOLD Study): a population-based prevalence study," Lancet, 2007, 370: 741-750.
Cradick et al., "COSMID: A Web-based Tool for Identifying and Validating CRISPR/Cas Off-target Sites," Mol Ther Nucleic Acids, 2014, 3: e214.
Drorbaugh and Fenn, "A barometric method for measuring ventilation in newborn infants," Pediatrics, 1955, 16: 81-87.
Duvoix et al., "Molecular pathogenesis of alpha-1-antitrypsin deficiency," Rev Mal Respir, Dec. 2014, 31(10):992-1002.
ElMallah et al., "Retrograde gene delivery to hypoglossal motoneurons using adeno-associated virus serotype 9," Human Gene Therapy Methods, Apr. 2012, 23: 148-156.
ElMallah et al., "Stimulation of Respiratory Motor Output and Ventilation in a Murine Model of Pompe Disease by Ampakines." American Journal of Respiratory Cell and Molecular Biology, 2015, 53: 326-335.
ElMallah et al., "Sustained correction of motoneuron histopathology following intramuscular delivery of AAV in pompe mice," Mol Ther, 2014, 22: 702-712.
Flotte et al., "Phase 2 Clinical Trial of a Recombinant Adeno-Associated Viral Vector Expressing alpha(1)-Antitrypsin: Interim Results," Hum Gene Ther, May 2011, 22: 1239-1247.
Grinnan and Truwit, "Clinical review: respiratory mechanics in spontaneous and assisted ventilation," Crit Care, Oct. 2005, 9: 472-484.
Heit et al., "Update of the human and mouse SERPINgene superfamily," Hum Genomics, 2013, 7(1): 22.
Laurell and Eriksson, "The electrophoretic alpha1-globulin pattern of serum in alpha1-antitrypsin deficiency," COPD, Mar. 2013, 10 (Suppl 1): 3-8.
Lomas and Silverman, "The genetics of chronic obstructive pulmonary disease," Respir Res, 2001, 2: 20-26.
Lomas et al., "Update on alpha-1 antitrypsin deficiency: New therapies," J Hepatol, Mar. 2016, 65: 413-424.
Lomask, "Further exploration of the Penh parameter," Exp Toxicol Pathol, Jun. 2006, 57 (Suppl 2): 13-20.
Lozano et al., "Global and regional mortality from 235 causes of death for 20 age groups in 1990 and 2010: a systematic analysis for the Global Burden of Disease Study 2010," Lancet, 2012, 380: 2095-2128.
Martorana et al., "The pallid mouse. A model of genetic alpha 1-antitrypsin deficiency," Lab Invest, Feb. 1993, 68: 233-241.
Mayer et al., "Occupational exposure risks in individuals with PI*Z alpha(1)-antitrypsin deficiency," Am J Respir Crit Care Med, 2000, 162: 553-558.
McGovern et al., "Evaluation of respiratory system mechanics in mice using the forced oscillation technique," J Vis Exp, May 2013, 75: e50172.
Mitzner and Tankersley, "Interpreting Penh in mice," Journal of Applied Physiology, 2003, 94: 828-831; author reply 831-832.
Papandrinopoulou et al., "Lung compliance and chronic obstructive pulmonary disease," Pulm Med, 2012, 2012: 542769.

(Continued)

*Primary Examiner* — Michael C Wilson
(74) *Attorney, Agent, or Firm* — Fish & Richardson P.C.

(57) ABSTRACT

Transgenic non-human animals, e.g., rodents, e.g., mice comprising genomic mutations that inactive all of the serpin1A genes and thus lack any functional serpinA1 genes. As a result of the genomic mutations, the animals express no hepatic or circulatory AAT protein. Also provided herein are cells and tissues derived from the transgenic mice.

7 Claims, 19 Drawing Sheets

Specification includes a Sequence Listing.

(56) References Cited

PUBLICATIONS

Paterson and Moore, "The expression and characterization of five recombinant murine alpha 1-protease inhibitor proteins," Biochem Biophys Res Commun, 1996, 219: 64-69.

Piitulainen et al., "Effect of age and occupational exposure to airway irritants on lung function in non-smoking individuals with alpha 1-antitrypsin deficiency (PiZZ)," Thorax, 1997, 52: 244-248.

Senn et al., "alpha1-Antitrypsin deficiency and lung disease: risk modification by occupational and environmental inhalants," Eur Respir J, 2005, 26: 909-917.

Stockley, "Alpha1-antitrypsin Review," Clin Chest Med, Mar. 2014, 35(1):39-50.

Strange or Beiko, "Treatment of Alpha-1 Antitrypsin Deficiency," Semin Respir Crit Care Med, Aug. 2015, 36(4):470-7.

Takahashi et al., "Imaging of pulmonary emphysema: a pictorial review," Int J Chron Obstruct Pulmon Dis, 2008, 3: 193-204.

Takubo et al., "Alpha1-antitrypsin determines the pattern of emphysema and function in tobacco smoke-exposed mice: parallels with human disease," Am J Respir Crit Care Med, 2002, 166: 1596-1603.

Teschler, "Long-term experience in the treatment of α1-antitrypsin deficiency: 25 years of augmentation therapy," Eur Respir Rev, Mar. 2015, 24(135):46-51.

Traclet et al., "Augmentation therapy of alpha-1 antitrypsin deficiency associated emphysema," Rev Mal Respir, Apr. 2015, 32(4):435-46.

Wang et al., "Deletion of Serpina1a, a murine alpha1-antitrypsin ortholog, results in embryonic lethality," Exp Lung Res, 2011, 37: 291-300.

Wang et al., "One-step generation of mice carrying mutations in multiple genes by CRISPR/Cas-mediated genome engineering," Cell, May 2013, 153(4):910-8.

Wang et al., "PacBio-LITS: a large-insert targeted sequencing method for characterization of human disease-associated chromosomal structural variations," BMC Genomics, 2015, 16: 214.

Yang et al., "Generating genetically modified mice using CRISPR/Cas-mediated genome engineering," Nat Protoc, 2014, 9: 1956-1968.

Borel et al., "Simultaneous disruption of five Serpina1 genes in mice using CRISPR/Cas9 to generate the first model of alpha-one antitrypsin deficiency, the leading cause of genetic COPD," Poster, Presented at the 2015 UMMS Research Retreat, Gene Therapy Center, University of Massachusetts Medical School, Worcester, MA (Oct. 8, 2015), 1 page poster available online at https://www.umassmed.edu/globalassets/mueller-lab-for-gene-therapy/images/blog-posts/2015-umms-aat.pdf.

Cox et al., "Simultaneous Disruption of Five SerpinA1 Genes in Mice Using CRISPR/Cas9 to Generate the First Animal Model of Alpha-1 Antitrypsin Deficiency", Molecular Therapy 23(Supp 1):S133, Abstract 333 (May 2015), 1 page.

Cox et al., "Simultaneous Disruption of Five SerpinA1 Genes in Mice Using CRISPR/Cas9 to Generate the First Animal Model of Alpha-1 Antitrypsin Deficiency", Poster, Presented at the American Society of Gene and Cell Therapy Annual Meeting, New Orleans, LA (May 16, 2015), 1 page, poster available online at https://www.umassmed.edu/contentassets/11e4532c8cd949019b7d410bfc670fa1/aat-ko-mouse-asgct-poster.pdf.

Borel et al., "Genome Editing to Generate the First Mouse Model of Alpha-One Antitrypsin Deficiency, the Leading Cause of Genetic COPD," Molecular Therapy 24(Supp 1):S65 (May 2016), 1 page.

* cited by examiner

| Stage | N | % |
|---|---|---|
| Injected oocytes | 461 | |
| Implanted oocytes | 304 | 66% |
| Total pups | 45 | 15% |
| Pups surviving passed newborn | 39 | 87% |
| Knockouts | 3 | 8% |

FIG. 1B

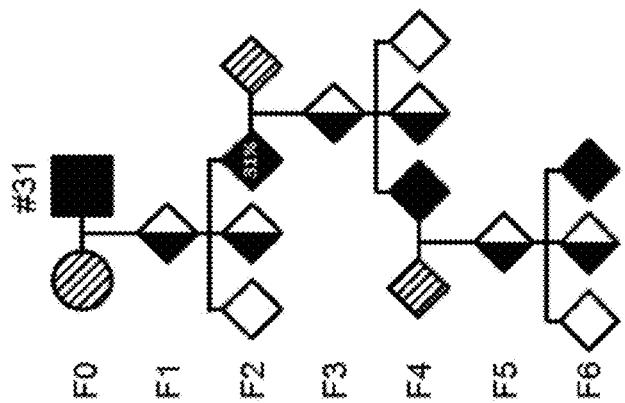
FIG. 1E
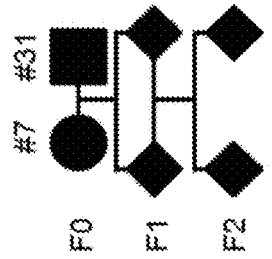
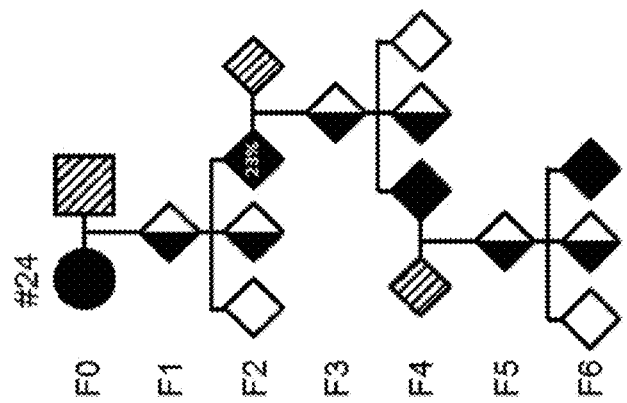
FIG. 1F
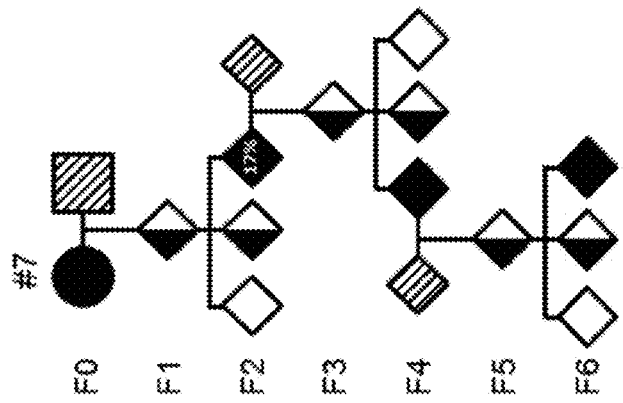

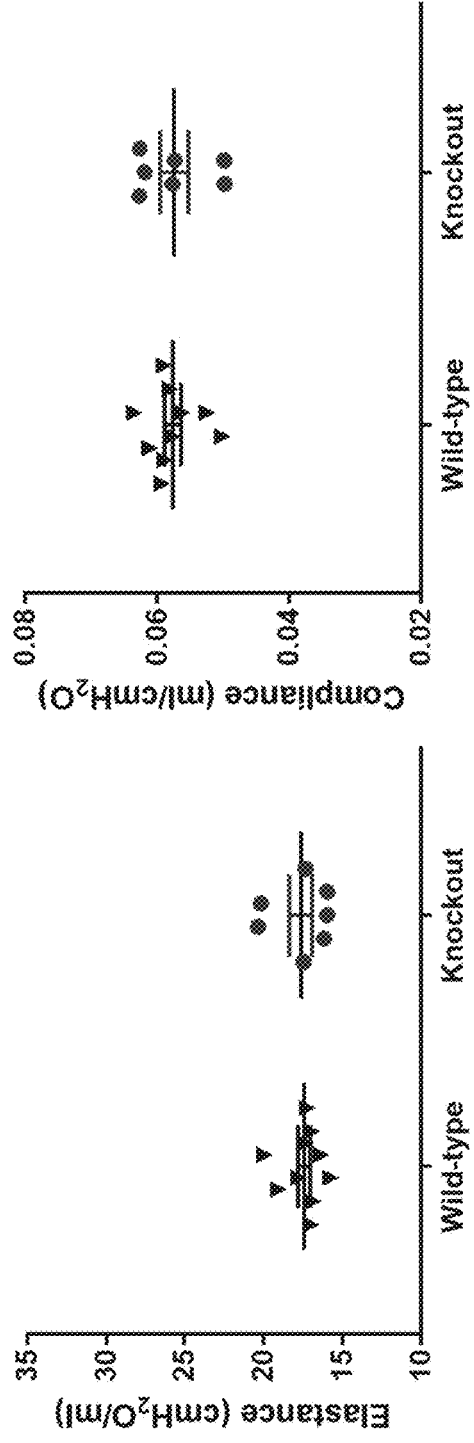
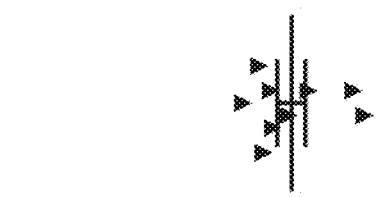
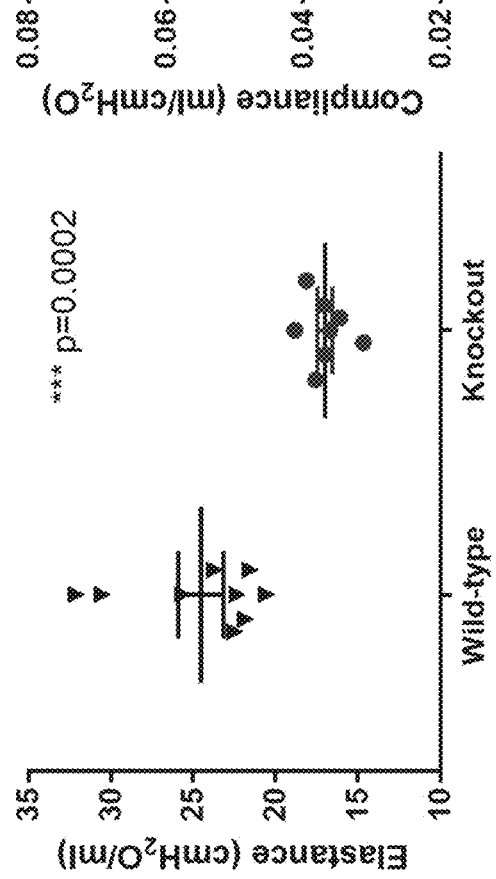
FIG. 6A  FIG. 6B  FIG. 6C  FIG. 6D

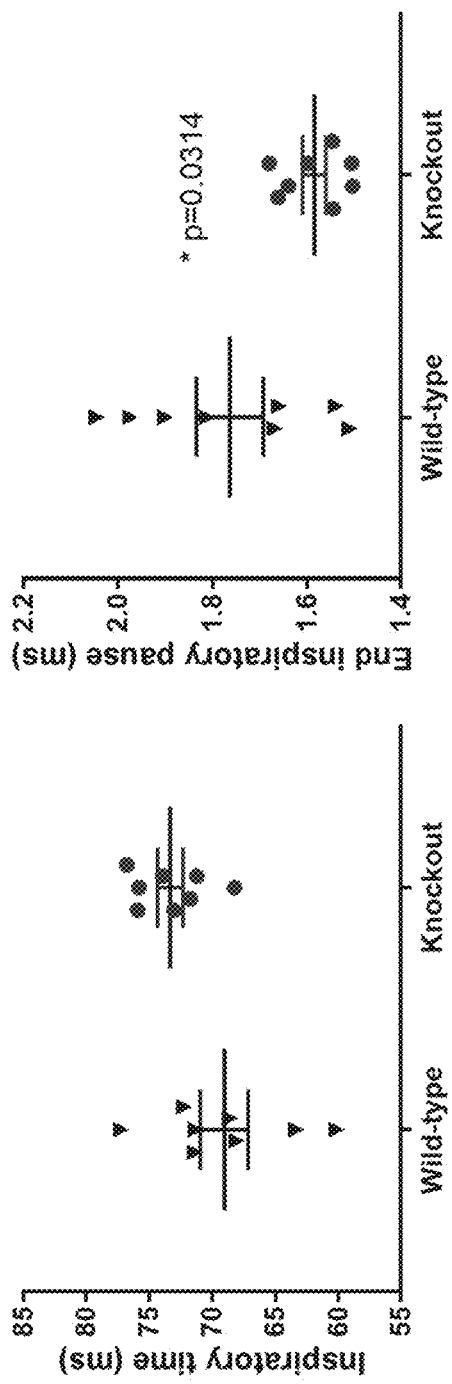
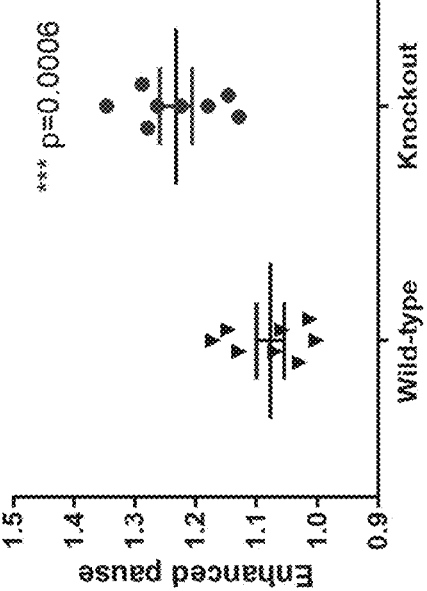
FIG. 6E
FIG. 6F
FIG. 6G

SEQUENCE LISTING

<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: guide RNAr10_ serpAcon181_159

<400> SEQUENCE: 1
ctgcagctga gcacaggcaa tgg                                              23

<210> SEQ ID NO 2
<211> LENGTH: 20
<212> TYPE: DNA
<213> ORGANISM: Artificial Sequence
<220> FEATURE:
<223> OTHER INFORMATION: guide RNAr10_ serpAcon181_159 without PAM

<400> SEQUENCE: 2
ctgcagctga gcacaggcaa                                                  20

<210> SEQ ID NO 3
<211> LENGTH: 23
<212> TYPE: DNA
<213> ORGANISM: Artificial Sequence
<220> FEATURE:
<223> OTHER INFORMATION: guide RNAf16_ serpAcon250_272

<400> SEQUENCE: 3
tttgtgtgag gttgaactgc agg                                              23

<210> SEQ ID NO 4
<211> LENGTH: 20
<212> TYPE: DNA
<213> ORGANISM: Artificial Sequence
<220> FEATURE:
<223> OTHER INFORMATION: guide RNAf16_ serpAcon250_272 without PAM

<400> SEQUENCE: 4
tttgtgtgag gttgaactgc                                                  20

<210> SEQ ID NO 5
<211> LENGTH: 23
<212> TYPE: DNA
<213> ORGANISM: Artificial Sequence
<220> FEATURE:
<223> OTHER INFORMATION: guide RNAf18_ serpAcon292_314

<400> SEQUENCE: 5
gagtgtcacc cttgctccct agg                                              23

<210> SEQ ID NO 6
<211> LENGTH: 20
<212> TYPE: DNA
<213> ORGANISM: Artificial Sequence
<220> FEATURE:
<223> OTHER INFORMATION: guide RNAf18_ serpAcon292_314 without PAM

<400> SEQUENCE: 6
gagtgtcacc cttgctccct                                                  20

<210> SEQ ID NO 7
<211> LENGTH: 23
<212> TYPE: DNA
<213> ORGANISM: Artificial Sequence

```
<220> FEATURE:
<223> OTHER INFORMATION: guide RNAf23_ serpAcon3280_350

<400> SEQUENCE: 7
aggctgtggc aatgctcact ggg                                          23

<210> SEQ ID NO 8
<211> LENGTH: 20
<212> TYPE: DNA
<213> ORGANISM: Artificial Sequence
<220> FEATURE:
<223> OTHER INFORMATION: guide RNAf23_ serpAcon3280_350 without PAM

<400> SEQUENCE: 8
aggctgtggc aatgctcact                                              20

<210> SEQ ID NO 9
<211> LENGTH: 18
<212> TYPE: DNA
<213> ORGANISM: Artificial Sequence
<220> FEATURE:
<223> OTHER INFORMATION: PCR forward primer

<400> SEQUENCE: 9
caaacctggg agactttg                                                18

<210> SEQ ID NO 10
<211> LENGTH: 18
<212> TYPE: DNA
<213> ORGANISM: Artificial Sequence
<220> FEATURE:
<223> OTHER INFORMATION: PCR reverse primer

<400> SEQUENCE: 10
agagtaggga acgtgatg                                                18

<210> SEQ ID NO 11
<211> LENGTH: 20
<212> TYPE: DNA
<213> ORGANISM: Artificial Sequence
<220> FEATURE:
<223> OTHER INFORMATION: PCR T7 promoter universal primer

<400> SEQUENCE: 11
taatacgact cactataggg                                              20

<210> SEQ ID NO 12
<211> LENGTH: 76
<212> TYPE: DNA
<213> ORGANISM: Artificial Sequence
<220> FEATURE:
<223> OTHER INFORMATION: PCR amplicon

<400> SEQUENCE: 12
aacatcttct tctccccagt gagcattgcc acagcctttg ctatgctctc cctagggagc   60
aagggtgaca ctcaca                                                  76

<210> SEQ ID NO 13
<211> LENGTH: 28
<212> TYPE: DNA
<213> ORGANISM: Artificial Sequence
<220> FEATURE:
<223> OTHER INFORMATION: PCR amplicon

<400> SEQUENCE: 13
```

```
gagctgcagc tgagcacagg caatggcc                                          28

<210> SEQ ID NO 14
<211> LENGTH: 20
<212> TYPE: DNA
<213> ORGANISM: Artificial Sequence
<220> FEATURE:
<223> OTHER INFORMATION: PCR amplicon

<400> SEQUENCE: 14
aacatcttct tctccccaca                                                   20

<210> SEQ ID NO 15
<211> LENGTH: 40
<212> TYPE: DNA
<213> ORGANISM: Artificial Sequence
<220> FEATURE:
<223> OTHER INFORMATION: PCR amplicon

<400> SEQUENCE: 15
aacatcttct tctccccagt gagcattgcc acagcctttg                             40

<210> SEQ ID NO 16
<211> LENGTH: 28
<212> TYPE: DNA
<213> ORGANISM: Artificial Sequence
<220> FEATURE:
<223> OTHER INFORMATION: PCR amplicon

<400> SEQUENCE: 16
ggcctgcagt tcaacctcac acaaacat                                          28

<210> SEQ ID NO 17
<211> LENGTH: 19
<212> TYPE: DNA
<213> ORGANISM: Artificial Sequence
<220> FEATURE:
<223> OTHER INFORMATION: PCR amplicon

<400> SEQUENCE: 17
aacatcttct tctccccag                                                    19

<210> SEQ ID NO 18
<211> LENGTH: 22
<212> TYPE: DNA
<213> ORGANISM: Artificial Sequence
<220> FEATURE:
<223> OTHER INFORMATION: PCR amplicon

<400> SEQUENCE: 18
cagttcaacc tcacacaaac at                                                22

<210> SEQ ID NO 19
<211> LENGTH: 16
<212> TYPE: DNA
<213> ORGANISM: Artificial Sequence
<220> FEATURE:
<223> OTHER INFORMATION: PCR amplicon

<400> SEQUENCE: 19
atgctcacac aaacat                                                       16

<210> SEQ ID NO 20
<211> LENGTH: 64
<212> TYPE: DNA
<213> ORGANISM: Artificial Sequence
```

```
<220> FEATURE:
<223> OTHER INFORMATION: PCR amplicon

<400> SEQUENCE: 20
caacacctcc tccaaaccct caacagacca gacagtgagc tgcagctgag cacaggcaat     60
ggcc                                                                 64

<210> SEQ ID NO 21
<211> LENGTH: 16
<212> TYPE: DNA
<213> ORGANISM: Artificial Sequence
<220> FEATURE:
<223> OTHER INFORMATION: PCR amplicon

<400> SEQUENCE: 21
gagcatagca atggcc                                                    16
```

MOUSE MODEL OF ALPHA-ONE ANTITRYPSIN (AAT) DEFICIENCY

CLAIM OF PRIORITY

This application claims priority under 35 USC § 119(e) to U.S. Provisional Patent Application Ser. No. 62/336,220, filed on May 13, 2016. The entire contents of the foregoing are hereby incorporated by reference.

STATEMENT OF FEDERALLY SPONSORED RESEARCH

This invention was made with government support under Grant Numbers NS088689, DK098252, and OD018259 awarded by the National Institutes of Health. The government has certain rights in the invention.

TECHNICAL FIELD

The present invention relates, at least in part, to transgenic non-human animals, e.g., rodents, e.g., mice comprising genomic mutations that inactive all of the serpin1A genes and thus lack any functional serpinA1 genes. As a result of the genomic mutations, the animals express no hepatic or circulatory AAT protein. Also provided herein are cells and tissues derived from the transgenic mice.

BACKGROUND

Alpha-one antitrypsin (AAT) deficiency is a common autosomal co-dominant genetic disorder. This condition affects 1:2500 individuals of European ancestry, leading to the development of lung and liver disease. Within North American and Northern European populations, an estimated 4% of individuals are carriers of mutant alleles. AAT deficiency presents with an emphysema phenotype in the lungs of older subjects. AAT deficient subjects can also suffer from liver disease of varying severity; however, lung disease is the principle cause of death. AAT is a protease inhibitor predominantly synthesized in the liver that belongs to the serine protease inhibitor (serpin) family. Upon secretion into the blood stream, AAT enters the lungs where it inactivates excess neutrophil elastase, thereby preventing damage to the alveoli. Mutations of the Serpina1 gene can lead to reduced serum levels of AAT and decreased protein functionality, allowing for unrestricted elastin breakdown, pulmonary inflammation and eventual emphysema. See, e.g., 1: Lomas et al., J Hepatol. 2016 Mar. 28. pii: S0168-8278(16)30083-6; Strange et al., Semin Respir Crit Care Med. 2015 August; 36(4):470-7; Traclet et al., Rev Mal Respir. 2015 April; 32(4):435-46; Teschler, Eur Respir Rev. 2015 March; 24(135):46-51; Duvoix et al., Rev Mal Respir. 2014 December; 31(10):992-1002; Stockley, Clin Chest Med. 2014 March; 35(1):39-50).

SUMMARY

Provided herein are transgenic mice whose genomes comprise homozygous or heterozygous inactivating mutations in Serpina1a, Serpina1b, Serpina1c, Serpina1d, and Serpina1e genes, and which express no hepatic or circulatory Alpha-One Antitrypsin (AAT) protein. In some embodiments, the inactivating mutations are in exon 2 of each of the genes, e.g., deletions in exon 2. The transgenic animals can be a mouse model of Alpha-One Antitrypsin (AAT)-deficiency lung disease, e.g., of COPD.

Also provided herein are isolated cells, tissues, or organs from the transgenic animals.

In another aspect, provided herein are methods for identifying a candidate compound for the treatment of Alpha-One Antitrypsin (AAT)-deficiency lung disease. The methods include contacting a transgenic animal as described herein, or a cell, tissue, or organ thereof, with a test compound; measuring levels of elastase in the animal, cell, tissue, or organ in the presence and absence of the test compound; and identifying a test compound that increases levels of elastase as a candidate compound.

Further, provided herein are methods of identifying candidate therapeutic compounds for the treatment of Alpha-One Antitrypsin (AAT)-deficiency lung disease. The methods include exposing a transgenic animal as described herein to a test compound; measuring one or more parameters of respiratory physiology, e.g., respiratory volume, inspiratory capacity, elastance, compliance, and/or quasi-static compliance. in the animal in the presence and absence of the test compound; and identifying a test compound that improves (increases) the one or more parameters as a candidate therapeutic compound.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-F. Generation of the Serpina1 knockout. (A) The five Serpina1 genes span a 230 kb region on chromosome 12 and their 11 kb sequence is highly homologous. Guide RNAs (gRNAs) were designed to target a conserved region in exon 2. (B) Statistics on the knockout generation from zygote injection to identification of the knockout line founders. (C) Pups were screened by PCR, and the 3 founders #7, #24 and #31 were identified by a decreased amplicon size. (D) PCR amplicons sequencing revealed various sequence deletion patterns created by combination of the 4 gRNAs; WT, SEQ ID NOs:12-13, A, SEQ ID NOs:13-14; WT, SEQ ID NOs:15, 16, and 13; B, SEQ ID NOs:17, 18, and 13; WT, SEQ ID NOs:15, 16, and 13; C, SEQ ID NOs: 17 and 13; WT, SEQ ID NOs:15, 16, and 13; D, SEQ ID NOs: 19 and 13; WT, SEQ ID NOs:15 and 20; E, SEQ ID NO: 21. (E) Breeding male founder #7 with female founder #31 demonstrated germline transmission. (F) Three independent founder lines were generated.

FIGS. 6A-G. Spontaneous emphysema in untreated Serpina1 knockouts. Pulmonary mechanics were assessed using a flexiVent in 35 weeks old (A-B) and 50 weeks old (C-D) wild-type mice (black triangles) and Serpina1 knockout mice (grey circles). Parameters assessed include elastance (A,C) and compliance (B,D). Whole body plethysmography was performed on unrestrained, unanesthetized 50 week old wild-type mice (black triangles) and Serpina1 knockout mice (grey circles) (E-G). Parameters assessed include inspiratory time (E), end expiratory pause (F), and enhanced pause (G). Statistical significance was determined by two-tailed unpaired t-test.

DETAILED DESCRIPTION

Figure 1A:
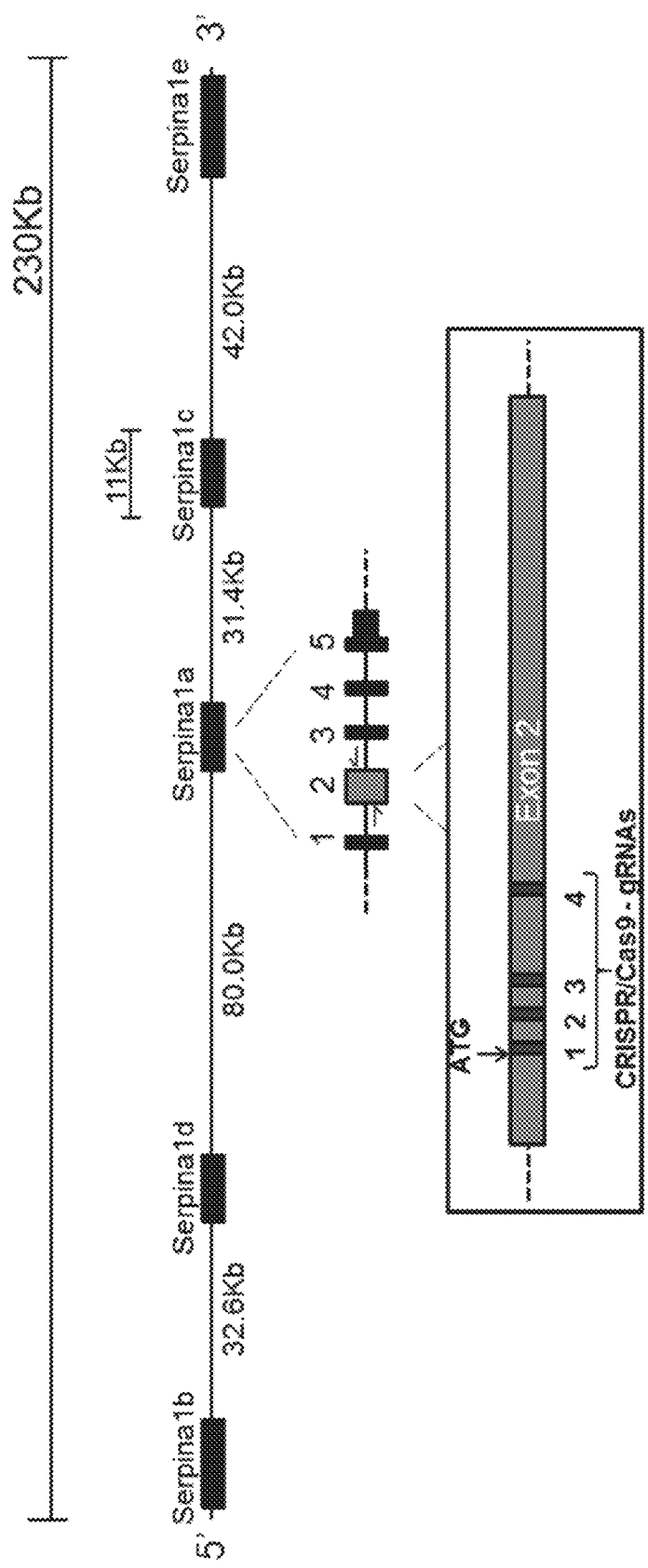

Chronic obstructive pulmonary disease (COPD) affects about 10% of the world population[1] and is the third leading cause of mortality worldwide[2]. While cigarette smoking and exposure to air particulates are well characterized environmental risk factors, α-1 antitrypsin (AAT) deficiency is the most common known genetic factor[3]. AAT deficiency is characterized by mutations in the SERPINA1 gene, resulting in reduced or inexistent levels of serum AAT protein[4], a protease inhibitor whose physiological target is neutrophil elastase. Low or no serum AAT therefore results in the unopposed action of neutrophil elastase on the alveolar interstitium. Clinically, AAT deficient patients present with pulmonary emphysema caused by damage to the walls between air sacs, resulting in fewer, larger air sacs and decreased gas exchange, which leads to increasing breathlessness. The current standard of care is weekly or biweekly intravenous infusion of recombinant AAT protein, although the disease is underdiagnosed and many patients will only start treatment once their respiratory capacity is already significantly and irreversibly affected. The endogenous protein is produced in the liver then circulates towards the lungs, therefore the only curative option available to date would be a lung transplantation combined with protein augmentation therapy. Lifelong weekly or biweekly infusions remain a burden for the patients, and alternative therapeutic options allowing for less frequent interventions are being actively investigated, those include gene therapy[5] and genome editing (Borel et al. submitted). The need for new therapeutics is however hindered by the absence of an animal model[6], with current study goals based on the FDA-defined endpoint of 11 μM serum AAT, instead of a physiologically relevant endpoint such as respiratory measurements, which may limit approval of valid candidates. This absence of animal model is due to the presence of Serpina1a-f paralogs in the murine genome[7], which made the generation of a full knockout a very difficult target using the traditional homologous recombination method. Recently, a murine Serpina1a knockout was unexpectedly described to be embryonically lethal[8]. Indeed, it is unclear why deleting one of several murine paralogs would be lethal while SERPINA1 null humans are viable. Prompted by this incongruity and the advent of CRISPR technology, we sought to confirm this surprising finding by generating a full knockout using guide RNAs (gRNAs) that target a sequence conserved in all Serpina1 genes. Herein is demonstrated the successful generation of the first murine Serpina1 complete knockout, which is viable and has a normal lifespan. This new mouse model presents a respiratory phenotype that recapitulates the human disease and therefore constitutes a true and robust model in which to validate novel therapeutics.

Currently, no animal model simulating the AAT-deficiency related lung condition exists; which severely limits the development of therapeutics. This is due to the higher genomic complexity of mice compared to humans: due to amplification events, C57BL/6 mice have five genes that are homologous to human SERPINA1.

The knockout mouse model presented here was generated using CRISPR targeting, and the evidence provided supports absence of AAT at genome, transcriptome, protein and functional levels. Additionally, and although the lung structure of mice is not fully identical to the lung structure of humans, knockout mice spontaneously develop emphysema with age, as shown by pulmonary mechanics and whole body plethysmography. Furthermore, the phenotype was consistently observed in all generations of three independent lines. This contradicts a previous report that claimed that deletion of Serpina1a was embryonically lethal[8]. Although it is unclear what the reason for this discrepancy may be, performing a simple transcriptome analysis on the previous model may be very informative and might reveal undetected off-target(s) that could have caused the embryonic lethality. Indeed, it should be pointed out that human SERPINA1 nulls are viable, and it therefore seems unlikely that it developed a function crucial for development during subsequent gene duplication in the mouse, particularly considering that the Serpina1 genes are 98% homologous[7].

It is well established that patients with α-1 antitrypsin deficiency are more likely to develop emphysema and/or develop it earlier if they are exposed to environmental inhalants, which include smoking (active or passive) and occupational exposure[16-18]. This first animal model of α-1 antitrypsin deficiency would therefore be highly relevant to further look into those findings, but also to test whether exposure to additional factors influences development of emphysema. These studies may provide safety data regarding occupational exposure to untested air particulates and new behaviors such as vaping (active and passive). This mouse model may therefore have a significantly impact on preventive health for the α-1 antitrypsin patient community, but also for the COPD population at large.

As described herein, the present inventors generated a quintuple gene knockout animal using CRISPR/Cas9 system via zygote microinjection. Three founding lines were generated in which all 5 copies of the gene were disrupted. Mice from all three lines demonstrate absence of hepatic and circulatory AAT protein as well as a reduced capability to inactivate neutrophil elastase. The lung phenotype was also characterized in response to a lipopolysaccharide challenge, where the model recapitulated many characteristics of the human lung disease including decreased elastance and increased compliance, and lung morphometry was also affected.

Thus provided herein are transgenic non-human animals, e.g., rodents, e.g., mice comprising genomic mutations that inactive all of the serpin1A genes and thus lack any functional serpinA1 genes. As a result of the genomic mutations, the animals express no hepatic or circulatory AAT protein. Also provided herein are cells and tissues derived from the transgenic mice. The mouse Serpin gene family is well-known; see, e.g., Heit et al., Hum Genomics. 2013; 7(1): 22. Exemplary sequences are as follows:

| Mus musculus SerpinA1 gene | NCBI Ref No. | |
| --- | --- | --- |
| | Protein | mRNA |
| Serpina1a, serine (or cysteine) peptidase inhibitor, clade A, member 1A | NP_033269.1 413 aa | NM_009243.4 |
| Serpina1b, serine (or cysteine) preptidase inhibitor, clade A, member 1B | NP_033270.3 413 aa | NM_009244.4 |
| Serpina1c, serine (or cysteine) peptidase inhibitor, clade A, member 1C | NP_033271.1 413 aa | NM_009245.2 |
| Serpina1d, serine (or cysteine) peptidase inhibitor, clade A, member 1D | NP_033272.1 413 aa | NM_009246.3 |
| Serpina1e, serine (or cysteine) peptidase inhibitor, clade A, member 1E | NP_033273.1 413 aa | NM_009247.2 |

A "transgenic animal" is a non-human animal, such as a mammal, generally a rodent such as a rat or mouse, in which one or more (preferably all) of the cells of the animal includes a transgene as described herein. Other examples of transgenic animals include non-human primates, sheep, dogs, cows, goats, chickens, amphibians, and the like. A "transgene" is exogenous DNA that is integrated into the genome of a cell from which a transgenic animal develops and thus remains in the genome of the mature animal, thereby directing the expression of an encoded gene product in one or more cell types or tissues of the transgenic animal. Knock-out animals, which include a gene deletion or mutation as described herein, are included in the definition of transgenic animals.

Methods for generating transgenic animals, particularly animals such as mice, via embryo manipulation and electroporation or microinjection of pluripotent stem cells or oocytes, are known in the art and are described, for example, in U.S. Pat. Nos. 4,736,866 and 4,870,009, U.S. Pat. No. 4,873,191, U.S. Ser. No. 10/006,611, "Transgenic Mouse Methods and Protocols (Methods in Molecular Biology)," Hofker and van Deursen, Editors (Humana Press, Totowa, N.J., 2002); and in "Manipulating the Mouse Embryo," Nagy et al., Editors (Cold Spring Harbor Laboratory Press, Cold Spring Harbor, N.Y., 2002), which are incorporated herein by reference in their entirety. Methods similar to those used to create transgenic mice can be used for production of other transgenic animals.

In general, in the present methods, a transgenic mouse as described herein is made by injecting a vector made as described herein into the pronucleus of a fertilized mouse oocyte and used for generation of a transgenic mouse with all of the SerpinA1 genes knocked out in all cells, using standard transgenic techniques, e.g., as described in "Transgenic Mouse Methods and Protocols (Methods in Molecular Biology)," Hofker and van Deursen, Editors (Humana Press, Totowa, N.J., 2002); U.S. Pat. Nos. 4,736,866 and 4,870,009, U.S. Pat. Nos. 4,873,191 and 6,791,006, and in Hogan, "Manipulating the Mouse Embryo," Nagy et al., Editors (Cold Spring Harbor Laboratory Press, Cold Spring Harbor, N.Y., 2002).

A transgenic founder animal can be identified based upon the presence of mutations in the SerpinA1 genes in its genome, for example by detecting the presence of the serpinA1 deletions/mutations directly, or by detecting the absence of AAT protein, e.g., in the liver or in the serum of the animal. For example, hepatocytes or fibroblasts can be used, such as embryonic fibroblasts or fibroblasts derived from the post-natal animal, e.g., the ear of the post-natal animal. A transgenic founder animal can then be used to breed additional animals carrying the transgene. Moreover, transgenic animals carrying the serpinA1 deletions/mutations can further be bred to other transgenic animals carrying other transgenes.

Methods for disrupting genes are known in the art. See, e.g., U.S. Pat. No. 7,022,893 to Takeda et al. and U.S. Pat. No. 6,218,595 to Giros et al., as well as U.S. Pat. No. 6,344,596 to W. Velander et al. (American Grey Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Grey Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to J. M. Hyttinin et al. (Pharming BV); U.S. Pat. No. 5,880,327 to H. Lubon et al. (American Grey Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Grey Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

In preferred embodiments, CRISPR/Cas9 gene editing methods are used to disrupt each of the five Serpin1A genes in the mice. See, e.g., Wang et al., Cell. 2013 May 9; 153(4):910-8

These animals (as well as cells and tissues derived therefrom) are useful, e.g., to study the processes associated with development and progression of respiratory disease, e.g., AAT-deficiency lung disease, e.g., emphysema, including the exacerbative effects of environmental toxins (e.g., cigarette smoke) and aging, as well as the ameliorative effects of potential therapeutics. Thus, provided herein are methods for evaluating the effect of a test compound on a parameter of respiratory physiology, e.g., respiratory volume, inspiratory capacity, elastance, compliance, and/or quasi-static compliance. The methods can include measuring the parameter in the animal, exposing the animal to the test compound (which could be an environmental factor such as a toxin), and then measuring the parameter in the animal during and/or after exposure. Other measures, such as levels of elastase, can be measured in cells from the animal.

Methods of Screening

The invention provides methods for identifying compounds, e.g., small organic or inorganic molecules (e.g., those with a molecular weight of less than 1,000 Da), oligopeptides, oligonucleotides, or carbohydrates, capable of replacing or increasing AAT activity. Such compounds can be useful in the treatment of lung disease, e.g., emphysema, e.g., AAT-deficiency lung disease.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, *Solid-Supported Combinatorial and Parallel Synthesis of Small-Molecular-Weight Compound Libraries*, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, β-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to AAT or a downstream effector of AAT. For example, in one embodiment, a general library of small molecules is screened, e.g., using the methods described herein, to select a first small molecule. Using methods known in the art, the structure of that small molecule is identified if necessary and correlated to a resulting biological activity, e.g., by a structure-activity relationship study.

As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate an increase in elastase in a cell from an animal describe herein, or stem cells or airway progenitor cells and or macrophages) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in treating respiratory disorders described herein. Thus, the invention also includes compounds identified as "hits" by a method described herein, and methods for their administration and use in the treatment, prevention, or delay of development or progression of a disease described herein.

In certain embodiments, screening methods of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 100,000 grams per mole, less than about 50,000 grams per mole, less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include proteins, peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp. (San Diego, Calif.). Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al., J. Med. Chem. (1994) 37:1385-1401; DeWitt and Czarnik, Acc. Chem. Res. (1996) 29:114; Armstrong et al., Acc. Chem. Res. (1996) 29:123; Ellman, Acc. Chem. Res. (1996)

29:132; Gordon et al., Acc. Chem. Res. (1996) 29:144; Lowe, Chem. Soc. Rev. (1995) 309; Blondelle et al., Trends Anal. Chem. (1995) 14:83; Chen et al., J. Am. Chem. Soc. (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of DeWitt et al., (Proc. Natl. Acad. Sci. USA, 90:6909-13 (1993)). Other synthesis methods, including the "tea-bag" technique of Houghten (see, e.g., Houghten et al., Nature, 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., J. Med. Chem., supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described herein.

EXAMPLES

The invention is further described in the following examples, which do not limit the scope of the invention described in the claims.

Methods

The following materials and methods were used in the Examples described below.

Animal Experiments

The institutional animal care and use committee at the University of Massachusetts Medical School approved all animal experiments. Mice were housed with 12-hour light/dark cycles on Bed-o'cob ¼" bedding (Andersons, Maumee, Ohio), and fed a standard laboratory diet. Lipopolysaccharide (LPS) challenge: male and female mice from the three lines (age 10-23 weeks) received two sequential orotracheal doses of LPS, 1 μg on day 1 and 0.5 μg on day 12 (serotype 055:B5 *Escherichia coli* LPS, L2880, Sigma-Aldrich, St Louis, Mo.) in 30 μl phosphate-buffered saline (PBS). The mice were anesthetized with an intraperitoneal dose of a ketamine/xylazine cocktail (90 mg/kg of ketamine and 4.5 mg/kg of xylazine) to sustain a surgical plan of anesthesia during the procedure. Animal were placed in dorsal recumbency on a rodent workstand (Braintree Scientific, Braintree, Mass.) and intubated. Following instillation, mice receives 2-3 ventilations with 0.2 ml of air. During the course of the challenge, the animals treated with LPS lost weight for ~3 days in response to the two doses (data not shown) and appeared slightly lethargic and with unkempt coats, this behavior was more evident in knockouts than wild-types. Daily treatment with subcutaneous saline sped up recovery.

Design and Validation of Guide RNAs

Guide RNAs (gRNAs) were designed and generated by the Mutagenesis Core (University of Massachusetts Medical School). The gRNAs were subsequently validated in vitro via single-strand annealing assay.

gRNAs targeting coding region of Mouse SerpinA1

| gRNA | Target | # | Target without PAM sequence | # |
|---|---|---|---|---|
| #1gRNAr10_serpAcon181_159 | CTGCAGCTGAGCACAGGCAATGG | 1 | CTGCAGCTGAGCACAGGCAA | 5 |
| #2gRNAf16_serpAcon250_272 | TTTGTGTGAGGTTGAACTGCAGG | 2 | TTTGTGTGAGGTTGAACTGC | 6 |
| #3gRNAf18_serpAcon292_314 | GAGTGTCACCCTTGCTCCCTAGG | 3 | GAGTGTCACCCTTGCTCCCT | 7 |
| #4gRNAf23_serpAcon3280_350 | AGGCTGTGGCAATGCTCACTGGG | 4 | AGGCTGTGGCAATGCTCACT | 8 |

, SEQ ID NO:

Zygote Microinjection

A total of 461 fertilized [C57BL/6(J) inbred-strain] oocytes were injected (Transgenic Animal Modeling Core, University of Massachusetts Medical School), divided over 6 injection sessions with a mixture of Cas9 messenger RNA (50 ng/µl final concentration) and four gRNAs species (f16, f18, f23 and r10; 20 ng/µl final concentration each). The injection utilized a continuous streaming needle to place approximately 100 pl of injection solution into the oocyte cytosol and nucleus. Of the 461 injected oocytes, 304 survived (66%) and underwent cell division when cultured overnight ex vivo. These embryos were implanted into a total of 13 pseudo-pregnant female recipients, giving rise to 45 pups, 39 of which survived the newborn period.

PCR Screening and Targeted Sequencing of Founders

Genomic DNA (gDNA) was isolated from earsnips (DNeasy Blood & Tissue Kit, Qiagen, Germantown, Md.) and the region of interested was amplified by PCR (forward primer: 5'-CAAACCTGGGAGACTTTG-3' (SEQ ID NO:9), reverse primer: 5'-AGAGTAGGGAACGTGATG-3' (SEQ ID NO: 10)). PCR products were run on a 1.5% agarose gel to assess absence of the predicted 610 bp wild-type amplicon. For #7, #24 and #31 which presented shorter amplicons, the amplicons were gel-extracted and cleaned (Qiagen), TOPO-TA cloned (Invitrogen, Carlsbad, Calif.), and DNA was isolated from the resulting clones and sequenced using a T7 promoter universal primer 5'-TAATACGACTCACTATAGGG-3' (SEQ ID NO: 11) (Eton Biosciences, Charlestown, Mass.).

ELISA

AAT levels in serum samples were quantified by direct ELISA. Briefly, serum proteins were immobilized in each well, and AAT was detected by incubating with a polyclonal goat anti-mouse AAT antibody (GA1T-90A-Z, ICL, Portland, Oreg.), followed by incubation with an HRP-conjugated rabbit anti-goat antibody (ICL) and a peroxidase substrate (KPL Scientific, Gaithersburg, Md.). $OD_{450nm}$ was read and a 4-parameter logistic model was fit to the standard curve (RS-90A1T, ICL), subsequently AAT concentration of the unknown samples was derived. Samples were run in technical triplicates.

Western Blot

Samples were prepared by incubating at 95° C. for 5 min 20 µl 20× diluted murine serum with 20 µl sample loading buffer (950 µl Novex Tris-Glycine SDS Sample buffer 2× (Life Technologies, Carlsbad, Calif.) with 50 µl 2-mercaptoethanol), and centrifuging at 12,000 rpm for 5 min. Samples (35 µl/well) were loaded in a 12% Tris-Glycine gel (Life Technologies), which was run for ~2 hr at 120V. Proteins were transferred onto a nitrocellulose membrane in 7 min at 20V (iBlot, Life Technologies). The membrane was blocked for 1 hr at RT in Odyssey Blocking Buffer in PBS (Li-Cor, Lincoln, Nebr.), then incubated overnight at 4° C. in primary antibody. The primary antibody against AAT was GA1T-90A-Z (ICL) and used at a dilution of 5:10,000; the primary antibody against albumin was ab85786 (Abcam, Cambridge, UK) and used at a dilution of 5:1,000. The membrane was subsequently washed 4×5 min in PBS-Tween, then incubated for 1 hr at RT in secondary antibody. The secondary antibodies were IRDye 680LT donkey anti-goat IgG (926-68024, Li-Cor) and IRDye 800CW donkey anti-rabbit IgG (926-32213, Li-Cor) and used at a dilution of 2:10,000. The washes were repeated and the membrane was imaged on a Li-Cor imager.

Neutrophil Elastase Assay

Relative serum neutrophil elastase activity was quantified by a colorimetric assay, according to the manufacturer's instructions (Enzo Life Sciences, Farmingdale, N.Y.). Briefly, neutrophil elastase was diluted in 37° C. assay buffer to 2.2 µU/µl. Elastinal (100 µM) or murine serum was added to each well followed by a 30 min incubation at 37° C. to allow inhibitor/elastase interaction. Substrate was subsequently added (100 µM) and absorbance $A_{450nm}$ was read every minute for 60 minutes. Data was analyzed by determining the slope of the kinetic for each sample, the slopes of the three technical replicates were averaged, values were reduced by subtracting the slope of the blank (buffer, substrate), and normalized by setting the control (buffer, substrate, elastase) at 100%.

Immunohistochemistry

FFPE liver sections (5 µm) from adult mice were incubated with 1:1000 goat-anti-mouse α-1 antitrypsin antibody (GA1T-90A-Z, ICL, Portland, Oreg.) for 1 hr, followed by 1:1000 HRP-conjugated horse-anti-goat IgG (PI-9500, Vector Labs, Burlingame, Calif.) for 1 hr. Several animals per line were analyzed, one representative example is showed.

Targeted Genome Sequencing

A 230 kb region of chromosome 12 (chr12:103,726,970-103,959,013) was sequenced by PacBio-large insert targeted sequencing (PacBio-LITS), following a protocol adapted from[22]. Briefly, high molecular weight gDNA was isolated from fresh liver tissue of adult mice (Genomic-tip 500, Qiagen), sheared to ~6 kb (g-TUBE, Covaris, Woburn, Mass.), pre-amplified, hybridized with custom probes (Roche Nimblegen, Madison, Wis.) designed based on mm10/GRCm38 for target enrichment by bead capture, and the captured libraries were amplified. Finally, SMRT libraries were constructed and sequenced on a PacBio instrument at the Yale Center for Genome Analysis (West Haven, Conn.). The adapter sequences were trimmed and low-quality reads were removed. PacBio sequencing generated >640000 clean reads for each sample. Sequence are assembled for each gene of each sample based on the alignment to the 230 kb target region.

RNA-Seq

Total RNA was isolated from snap-frozen liver tissue of 10 week old male mice using Trizol (Life Technologies) following the manufacturer's instructions. Barcoded libraries were sequenced as 50 nt single end reads on an Illumina HiSeq 4000 instrument at the Beijing Genomics Institute (BGI, Shenzhen, China). The adapter sequences were trimmed, and low-quality reads were removed. RNA-Seq generated >50 million clean reads for each sample. Using TopHat2, at least 70% of the clean reads mapped at a single location of the mouse reference genome (mm10) for each replicate sample. Normalization and differential expression gene analysis were performed with DESeq2 software package.

Plethysmography

Ventilation was quantified using whole-body plethysmography in unrestrained, unanesthetized mice. Mice were placed inside a 3.5"×5.75" Plexiglas chamber, which was calibrated with known airflow and pressure signals before data collection. Data was collected in 10-second intervals, and the Drorbaugh and Fenn equation[23] was used to calculate respiratory volumes including tidal volume and minute ventilation as previously described[24-26]. During the acclimation and baseline period of 2 hours, mice were exposed to normoxic air (21% $O_2$, balance $N_2$). At the conclusion of the baseline period, the mice were exposed to a brief respiratory challenge, which consisted of a 10-minute hypercapnic exposure (7% $CO_2$, 21% $O_2$, balance $N_2$).

FlexiVent

Measurements of pulmonary mechanics were performed using forced oscillometry (flexiVent system, SCIREQ, Montreal, Canada). Forced oscillometry was performed in intubated and anesthetized mice. Mice were anesthetized with an intraperitoneal injection (i.p.) injection of a ketamine (90 mg/kg) and xylazine (4.5 mg/kg) mixture. Following an adequate plane of anesthesia (loss of withdrawal to toe pinch), tracheotomy was performed, and a pre-calibrated cannula was introduced into the trachea. The mouse was then placed on a computer controlled piston-ventilator flexiVent system (SCIREQ) and ventilated at a tidal volume of 10 ml/kg, rate of 150 breaths/minute and a positive end expiratory pressure of 3 mmHg. Neuromuscular blockade with pancuronium bromide (2.5 mg/kg) was given to prevent spontaneous respiratory effort. Respiratory mechanics were obtained and calculated using flexiWare software (SCIREQ) as previously described[27]. In brief, measurements were obtained by analyzing pressure and volume signals acquired in reaction to predefined, small amplitude, oscillatory airflow waveforms (perturbations) applied to the subject's airways. First a "snapshot perturbation" maneuver was imposed to measure resistance (R), compliance (C), and elastance (E) of the whole respiratory system (airways, lung, and chest wall). Forced oscillation perturbation ("primewave-8") was consequently applied, and resulted in Rn, inertia of the air, tissue damping (resistance, G), H, and tissue hysteresivity (tissue damping [G]/H). Next, maximal PV loops were generated to obtain maximal vital (total) lung capacity (TLC), inspiratory capacity (IC) from zero pressure, form of deflating PV loop (K), static C (Cst), static elastance (Est), and hysteresis (area between inflating and deflating part of the loop). All maneuvers and perturbations were performed until three correct measurements were achieved. For flexiVent perturbations, a coefficient of determination of 0.95 was the lower limit for accepting a measurement. For each parameter, a total of three accepted measurements were calculated, and the average of the three technical replicates is used in data representation.

Morphometry

Immediately following measurements of lung mechanics (flexiVent) while still under anesthesia, lungs were harvested for morphometric analysis as previously described (Paxson et al. 2011, Hoffman et al. 2013). Briefly, the chest was opened, and the pulmonary circulation flushed via right ventricular puncture with 10 ml cold PBS. The degassed lung was inflated with 1% ultra-low temperature gel agarose (Sigma-Aldrich) in neutral buffered formalin (10%) to 25 cm pressure. Once fixed, lung volume was measure by water displacement (Paxson et al. 2011). Subsequently, lung tissues were oriented randomly in cassettes and embedded in paraffin, followed by random sectioning (10 µm thickness). Slides were stained with hematoxylin and eosin and 10 randomly oriented non-overlapping fields from each section were photographed, and MLI calculated as described.

Example 1. Generation of the Serpina1 Knockout

Figure 1C:
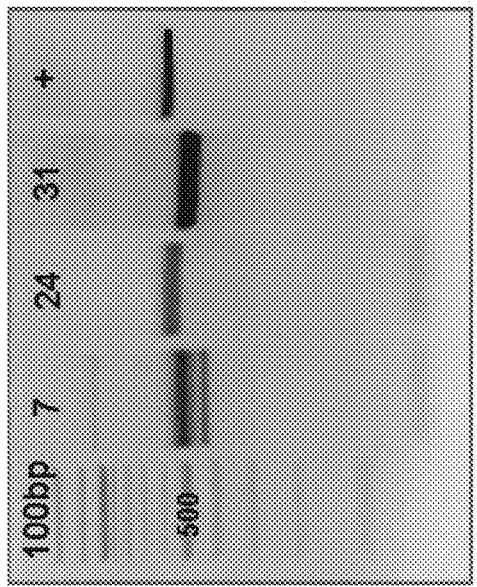
Figure 1D:
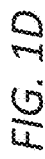

Six Serpina1 genes exist in the murine genome, designated in the current nomenclature as Serpina1a through Serpina1f. The genes are 11 kb-long, and span about 230 kb on chromosome 12. In our mouse strain of choice C57BL/6J, the first five Serpina1 genes (A-E) are present and expressed[7]. The corresponding proteins are designed α-1-antitrypsin (AAT) 1-1 through 1-5. Of these, AAT 1-1 and AAT 1-2 inhibit both neutrophil and pancreatic elastases, while AAT 1-3 and AAT 1-4 do not, and AAT 1-5 is not well characterized[9]. Four gRNAs were designed in a region conserved in all Serpina1 paralogs, exon 2 (FIG. 1A), and validated in vitro with a single strand annealing assay. Genetically modified mice were generated using the method described in[10]. Briefly, zygotes were microinjected with Cas9 mRNA and all four gRNAs, and subsequently implanted in 13 pseudopregnant females. A total of 45 pups were born, of which 87% survived (FIG. 1B) and were screened by PCR amplification of exon 2 (FIG. 1C). PCR amplicons were sequenced to identify the double-strand break sites for each gRNA. Various deletion patterns were created by combination of the different gRNAs and are highlighted in FIG. 1D. Deletion patterns include gRNA1-gRNA2, gRNA1-gRNA3 and gRNA1-gRNA4 (FIG. 1D). Out of the 39 viable animals, three were identified as knockout, two males and one female, subsequently referred to as #7, #24 and #31. Germline transmission was demonstrated when crossing founders #7 and #31 lead to 100% of the progeny to be knockouts (FIG. 1E). The founders were independently backcrossed twice (FIG. 1F) to get rid of hypothetical undesired genomic alterations due to CRISPR-related off-target effects, which lead to the generation of three independent lines of Serpina1 knockouts termed 7A, 24B and 31C (or A, B, and C) for founders #7, #24 and #31 respectively.

Example 2. Phenotypic and Functional Characterization

Figure 2A:
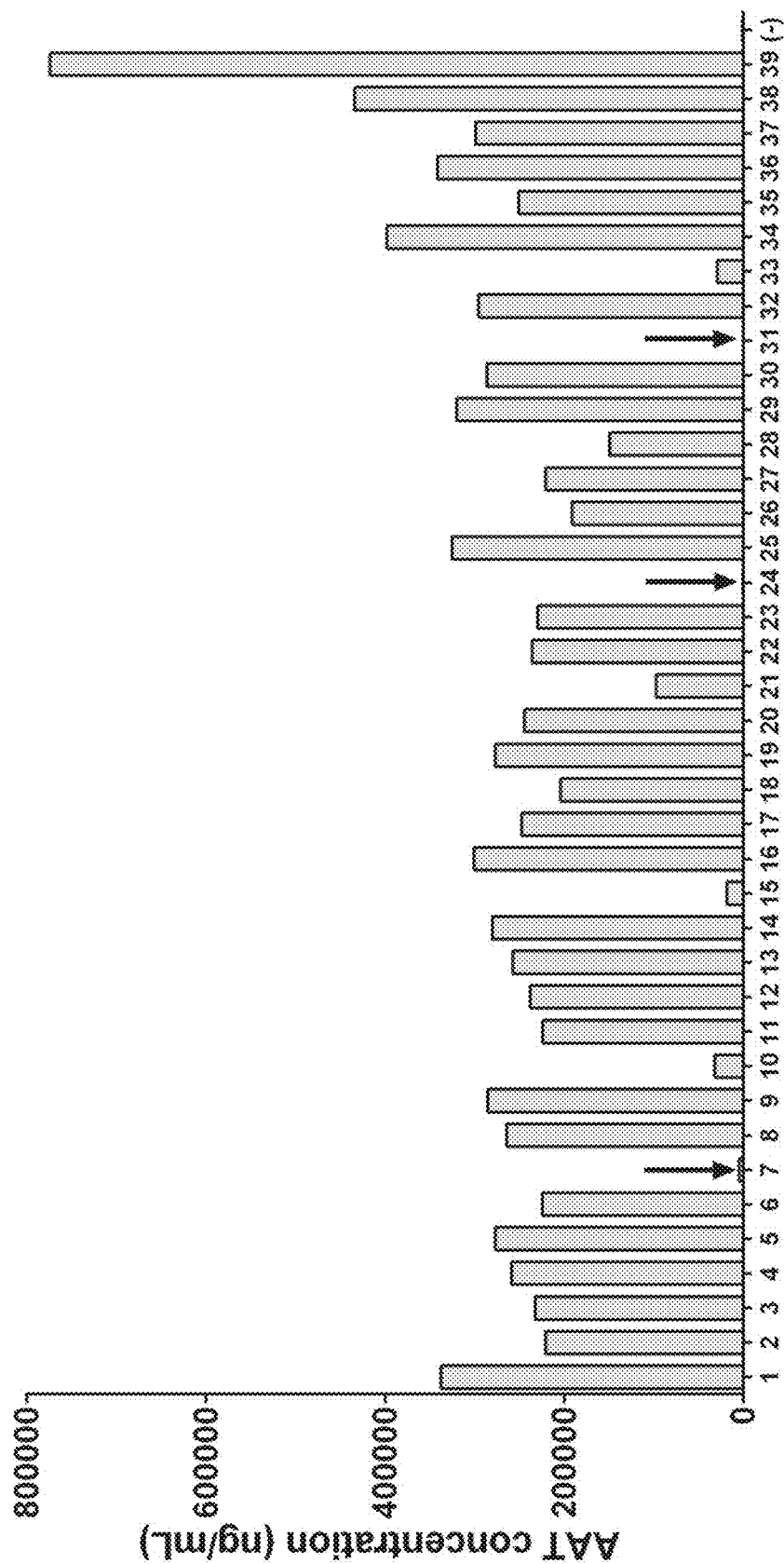
FIGS. 2A-D. Phenotypic and functional characterization. The serum of the three founders was devoid from AAT protein, as determined by ELISA (A) and western blot (B). (C) Immunohistochemistry shows absence of signal in liver tissue from knockout animals. (D) Serum from the three founders has reduced anti-elastase activity, as determined by quantification of the neutrophil elastase activity. C57M: male wild-type mouse; 7M: male founder #7; 24M: male founder #24; 31F: female founder #31; C57F: female wild-type mouse; AAT control: commercial pooled mouse serum.
Figure 2B:
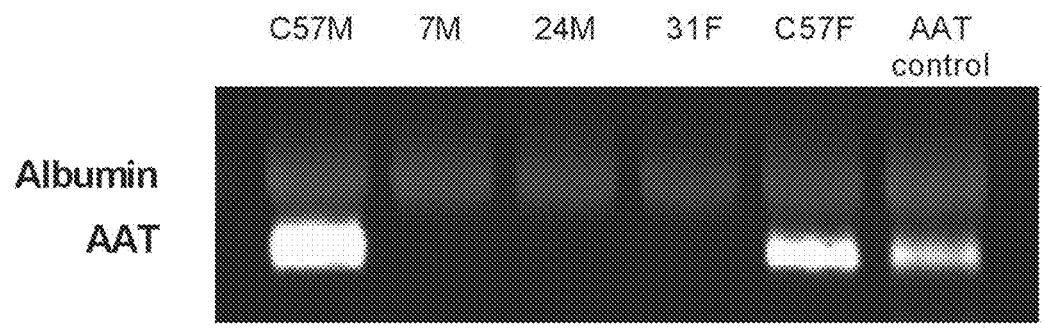
Figure 2C:
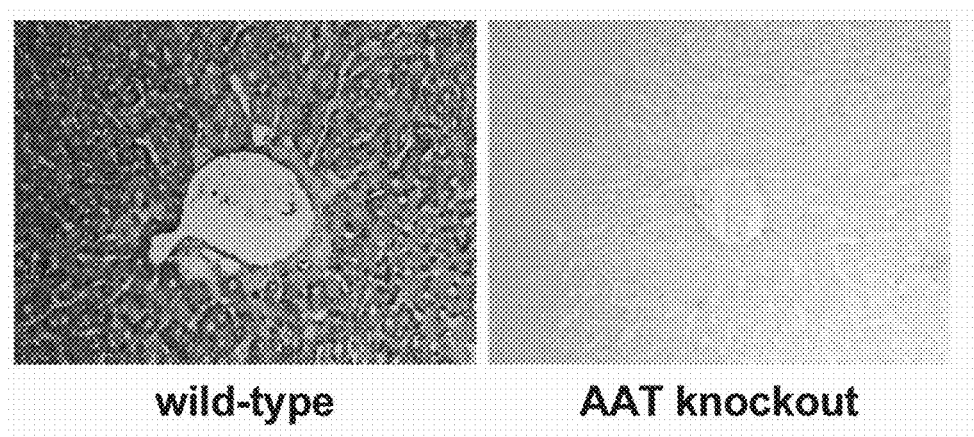
Figure 2D:
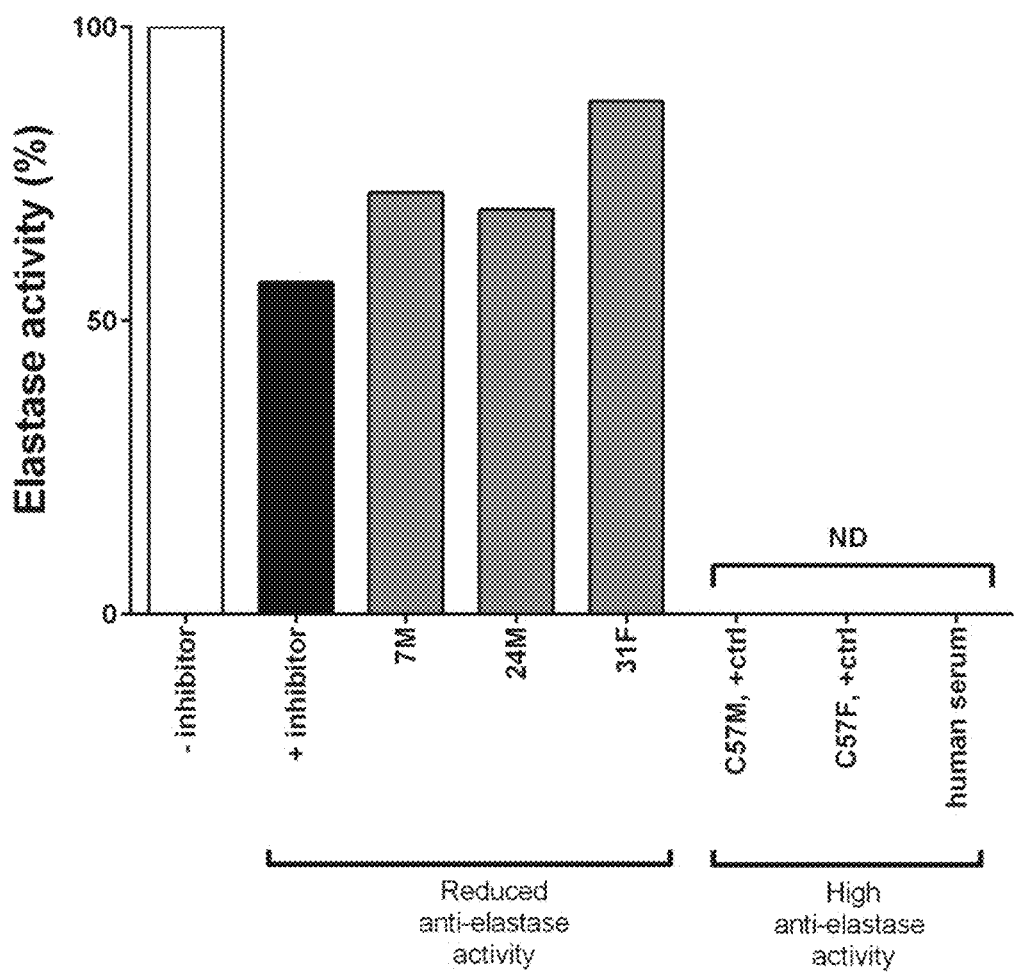

AAT is produced in the liver, secreted in the bloodstream and eventually reaches its main site of action, the lungs. There, it will protect the lung alveoli from destruction by neutrophil elastase by inactivating it. To assess whether the protein was present in the circulation, blood serum was sampled from all 39 animals and analyzed by indirect ELISA using an anti-mouse AAT primary antibody. The three founders demonstrated undetectable levels of AAT (FIG. 2A), confirming the results of the PCR screening. Blood serum from the founders was also analyzed by western blot, and similarly no AAT could be detected in these samples (FIG. 2B). Next, liver sections were subjected to immunohistochemical staining. While a strong staining reflects the high abundance of hepatic AAT in wild-type mice, the AAT knockout mice revealed a complete lack of staining denoting absence of the protein (FIG. 2C). Finally, we assessed through an elastase activity assay whether any physiological function of the protein could be detected. Blood serum was incubated with neutrophil elastase and its substrate, and relative elastase activity was derived from a colorimetric quantification of the kinetics of substrate degradation. While serum from wild-type male and female C57BL/6 mice exhibited a high capacity to inhibit neutrophil elastase, serum from the three founders showed a reduced capacity to do so (FIG. 2D, grey bars). The capacity to inhibit neutrophil elastase was even more reduced in the serum samples from the three founders than when using a commercial elastase inhibitor (FIG. 2D, black bar). This indicates that absence of serum AAT shown in FIGS. 2A,B translates to a loss of its physiological anti-elastase function.

Example 3. Genomic and Transcriptomic Characterization

Genomic alterations were characterized by targeted sequencing. Briefly, high molecular weight genomic DNA (gDNA) was isolated from liver tissue of one knockout mouse per founder line. This gDNA was subsequently sheared to a size of ~6 kb, and fragments of interest were pulled down using probes specific to the 230 kb region of interest, as shown in FIG. 1A. The ~2 kb captured fragments were sequenced by long-read PacBio sequencing, to allow for discrimination between highly homologous Serpina1 paralogs.

Figure 3:
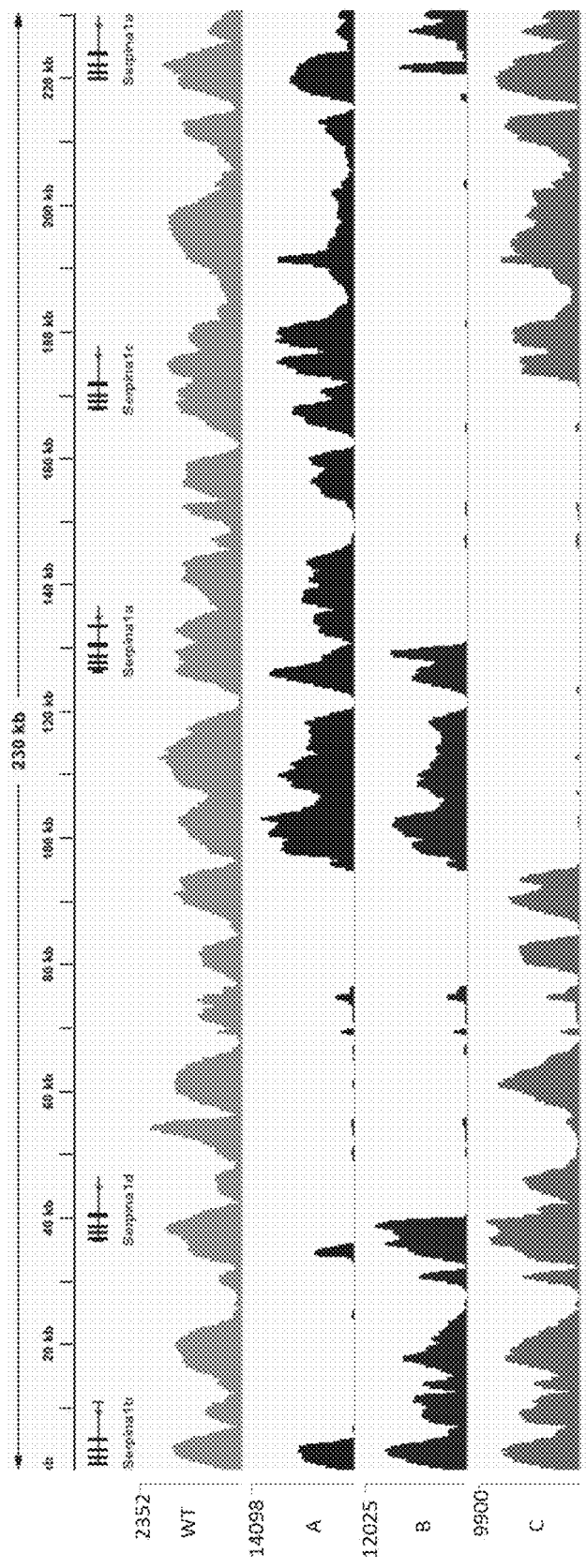
FIG. 3. Read quantification. Read coverage plot of the targeted region (230 kb) with four samples: WT (wild type), A (line 7A), B (line 24B), C (line 31C).

Next, RNA was isolated from liver tissue of four mice from generation F4, line 7A, four mice from generation F4, line 24B, and five C57BL/6 mice (all mice were 10 week old males; founder #31 being female the 31C line is at an earlier generation and was therefore not included in this analysis) and sequenced by 50SE sequencing. Sequencing depth is shown in FIG. 3.

The coordinates of the deleted region were determined for each line where the entire genomic sequence was deleted from the region of Chromosome 12 for which we did the targeted sequencing. These regions include intergenic regions as well as some of the gene variants:
Line 7A: 103731445-103822024
Line 24B: 103766358-103822013; 103856361-103947919
Line 31C: 103822846-103899744
All are in Chr12, with reference to genome build mm10.

A total of 231 genes were dysregulated in line 7A: 126 upregulated genes and 105 downregulated genes. A total of 299 genes were dysregulated in line 24B: 133 upregulated genes and 166 downregulated genes. The Serpina1 genes were the top downregulated genes in line 7A: Serpina1a by 0.0438 fold (adjusted sp-value 2.43E-196), Serpina1b by 0.0294 fold (adjusted p-value 3.24E-279), Serpina1c by 0.0027 fold (adjusted p-value 0), Serpina1d by 0.0058 fold (adjusted p-value 0), and Serpina1e by 0.0866 fold (adjusted p-value 6.18E-100). They were also in the top downregulated genes in line 24B: Serpina1a by 0.0325 fold (adjusted p-value 5.71E-302), Serpina1c by 0.0020 fold (adjusted p-value 0), Serpina1d by 0.0051 fold (adjusted p-value 0), and Serpina1e by 0.2338 fold (adjusted p-value 1.57E-08). As expected based on the genomic characterization on line 24B, reads mapping to Serpina1b were not decreased (fold change 0.9916; adjusted p-value 0.9869). In total, 106 genes were dysregulated in line 7A and line 24B jointly, 48 were up-regulated and 58 were down-regulated including 4 of the Serpina genes (a-c-d-e).

Off-targets for all 4 gRNAs were predicted using two independent algorithms: Cas OFFinder[11] and COSMID[12] and all results were compiled. Results from these predictions were cross-referenced with the list of dysregulated genes. No predicted off-target genes were identified as being dysregulated. This supports the view that the described phenotype is not due to CRISPR off-targeting.

Example 4. Induced Emphysema Following a Two-Hit, Two-Week LPS Challenge

Figure 4A:
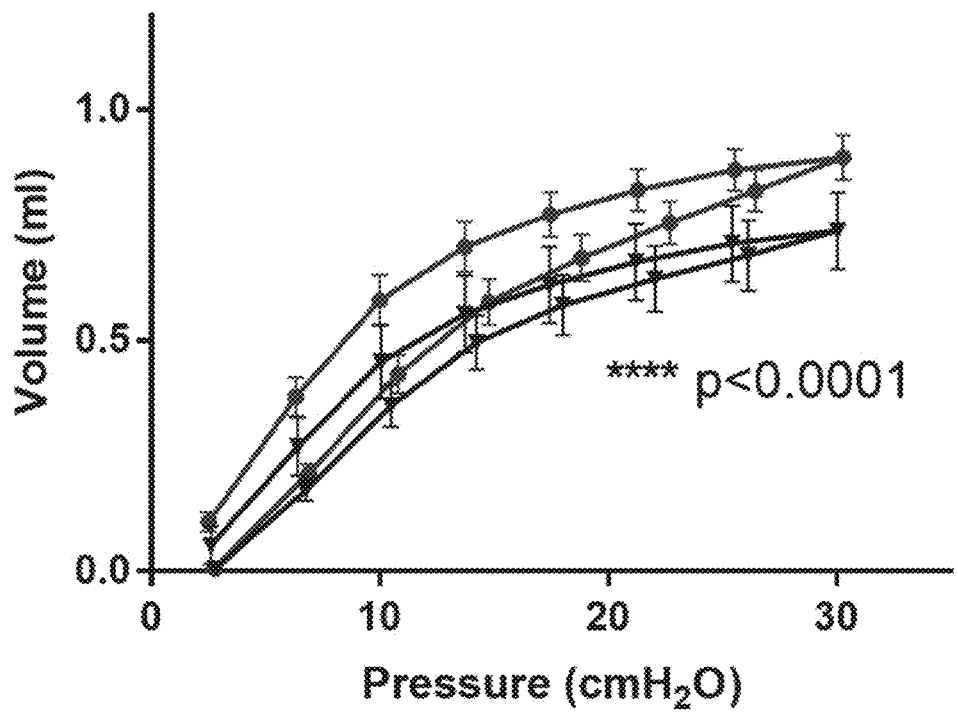
FIGS. 4A-E. Induced emphysema following a two-hit, two-week LPS challenge. Wild-type mice (black triangles) and Serpina1 knockout mice (grey circles) were both treated twice with lipopolysaccharide (LPS) and presence of emphysema was assessed two weeks after the first LPS dose. Pulmonary mechanics were determined using a flexiVent, parameters assessed include (A) pressure-volume (PV) loop, (B) inspiratory capacity, (C) quasi-static compliance. Fixed lung tissue was stained by H&E (D) and the morphometry was analyzed and the mean linear intercept quantified (E). Statistical significance was determined by two-tailed unpaired t-test, except for the PV loop (2-way ANOVA).
Figure 4B:
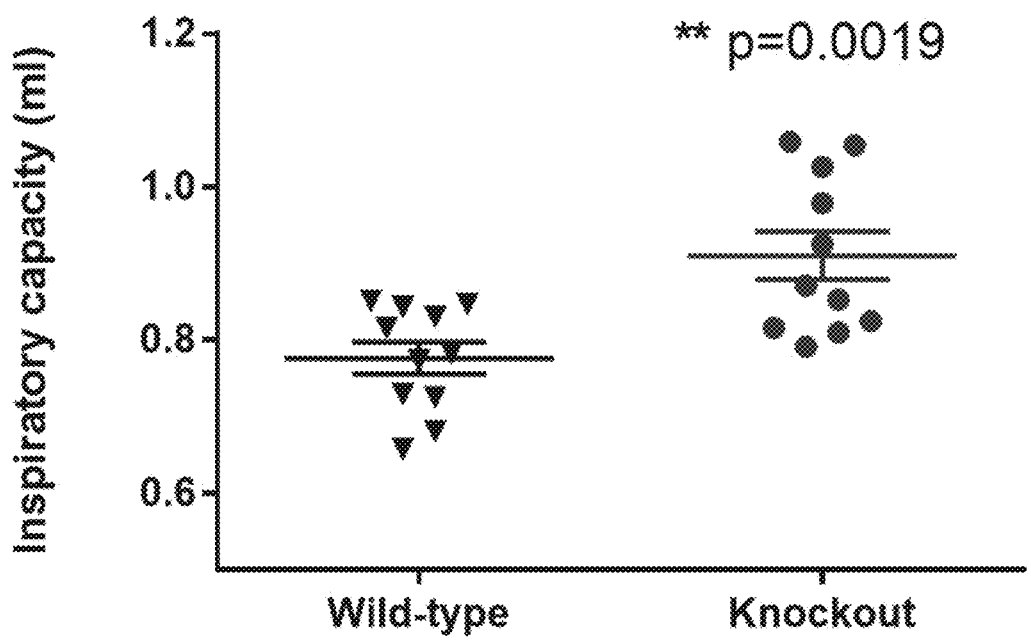
Figure 4C:
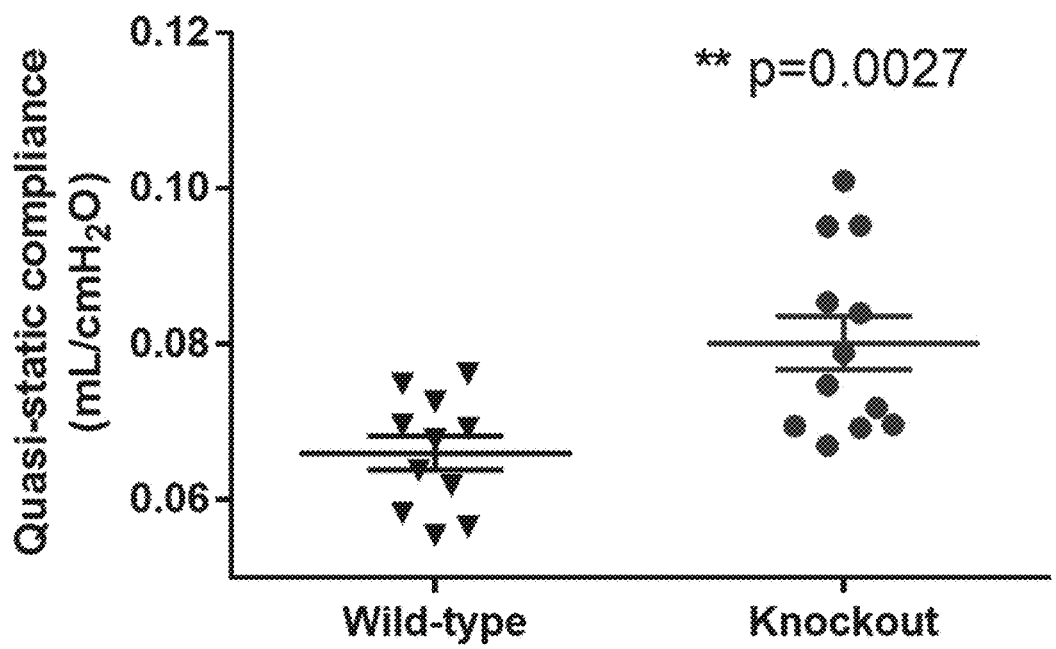
Figure 4D:
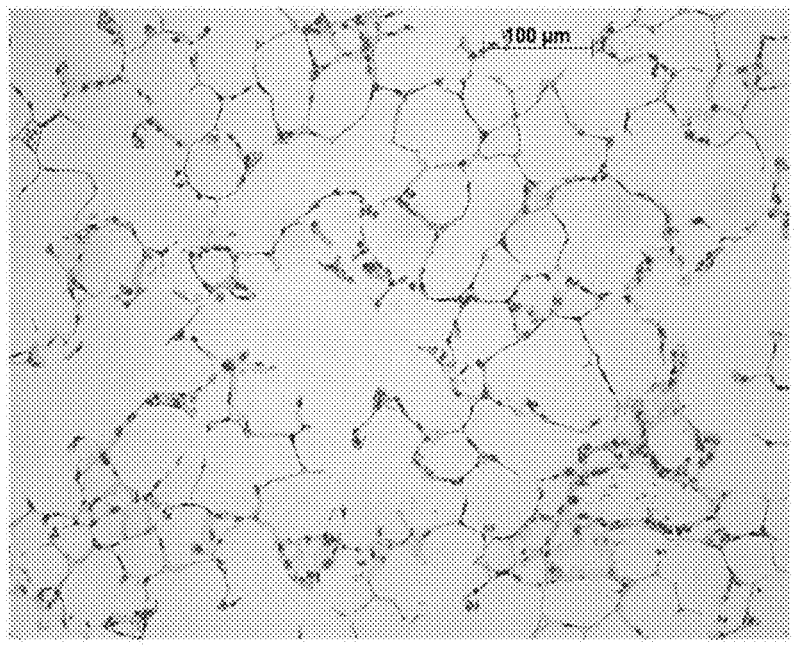
Figure 4E:
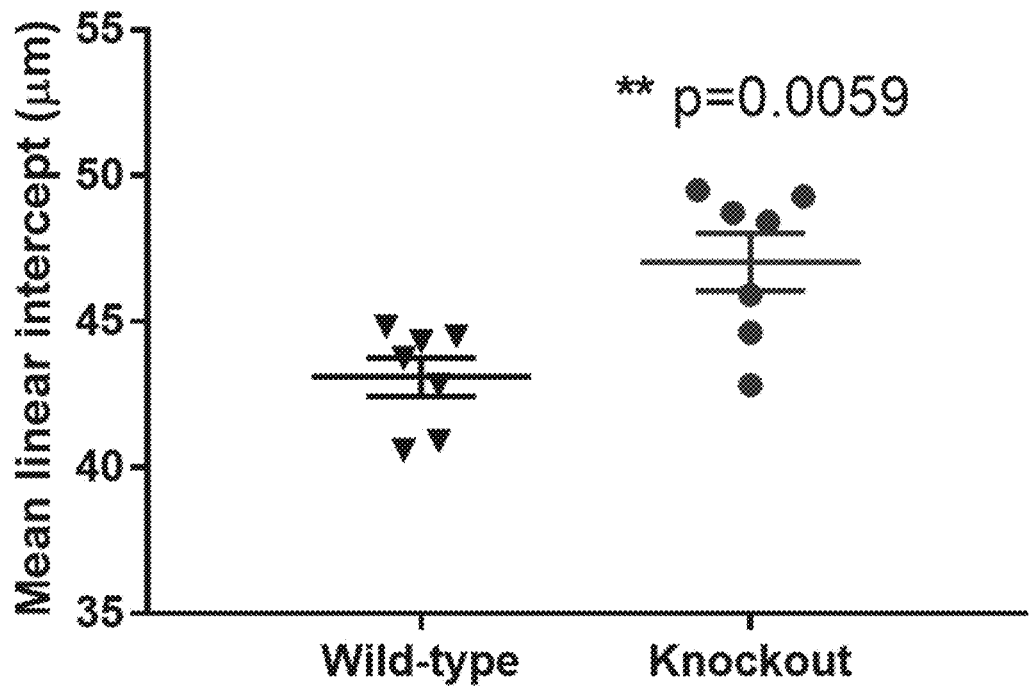
Figure 4F:
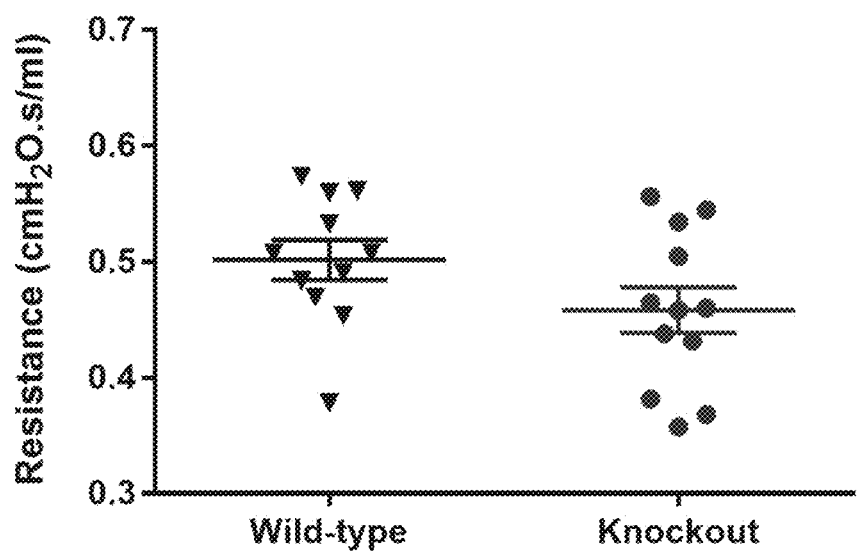
FIGS. 4F-I. Induced emphysema following a two-hit, two-week LPS challenge. Wild-type mice (black triangles) and Serpina1 knockout mice (grey circles) were both treated twice with lipopolysaccharide (LPS) and presence of emphysema was assessed two weeks after the first LPS dose. Pulmonary mechanics were determined using a flexiVent, parameters assessed include (F) resistance, (G) elastance, (H) compliance. (I) The total lung volume was determined. Statistical significance was determined by two-tailed unpaired t-test.
Figure 4G:
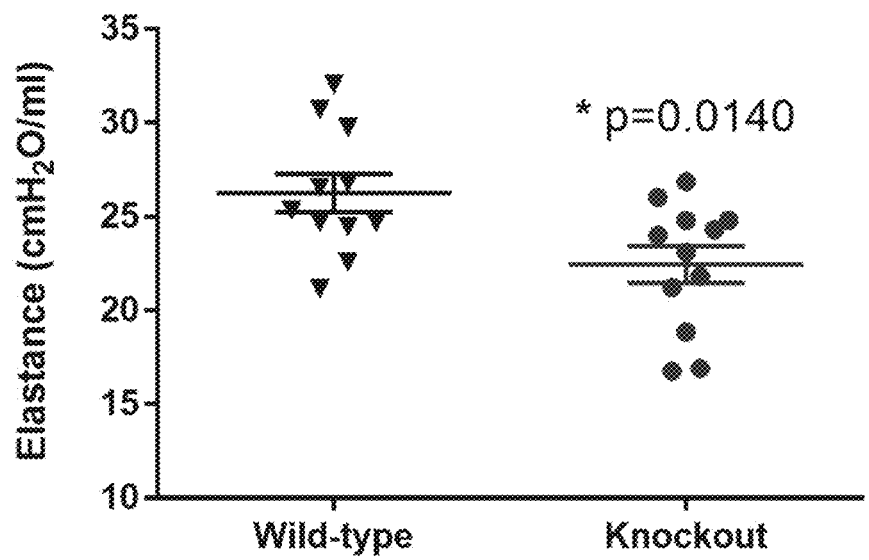
Figure 4H:
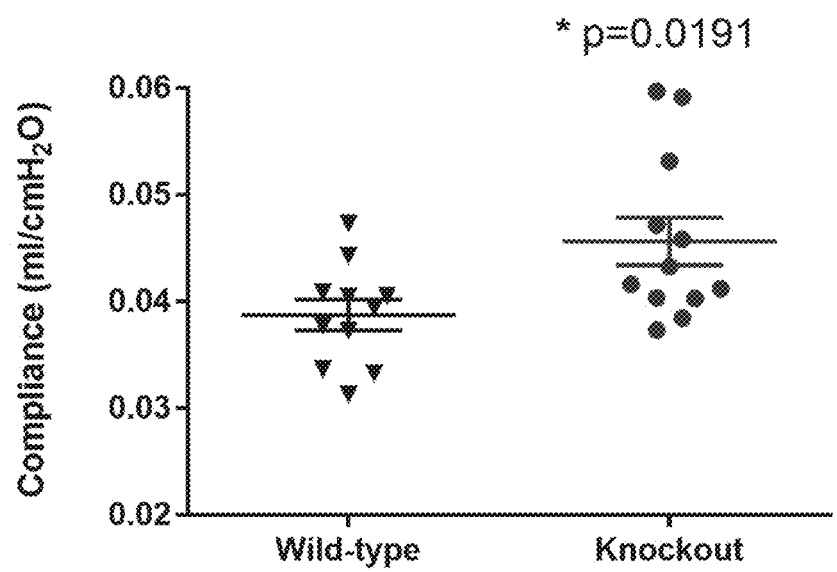
Figure 4I:
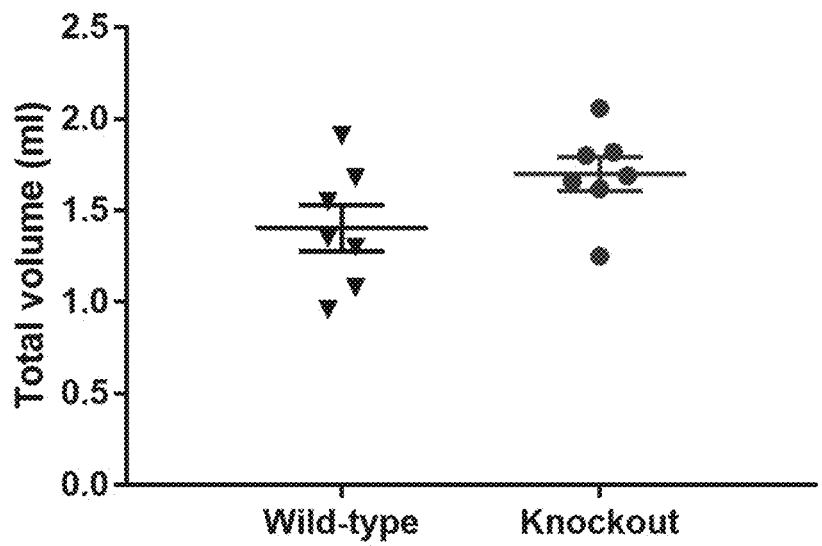

For the mock bacterial challenge, mice (n=11-12 per group) received two doses of LPS on day 1 and day 12 before characterization of their pulmonary mechanics and lung morphometry at the end of the second week (FIGS. 4A-I). At endpoint, maximal pressure-volume (PV) loops were generated using ramp pressure-regulated perturbations, and the knockout PV loop was highly different from the wild-type PV loop (FIG. 4A). In line with that result, the inspiratory capacity of the knockouts was significantly increased by 17% from 0.78 ml to 0.91 ml (FIG. 4B). Resistance which is a measure of lung constriction was not significantly affected (wild-type group 0.50 cm $H_2O.s/ml$, knockout group 0.46 cm $H_2O.s/ml$, FIG. 4A). Next, several pulmonary mechanics parameters which are clinically well-characterized in emphysema were quantified. Elastance quantitatively assesses the elastic rigidity of the lungs, and in patients the loss of elastic recoil is a characteristic of emphysema[13]. In this experiment, the dynamic elastance was significantly decreased by 15%, from 26.2 6 cm $H_2O/ml$ in the wild-types to 22.45 cm $H_2O/ml$ in the knockouts, which indicated less stiffness (FIG. 4G), and is consistent with emphysema. An increase in dynamic compliance, which is the reciprocal of elastance, is typical of emphysema in patients[13]. In this experiment, compliance was significantly increased in the knockouts (FIG. 4H) which means that their lungs can be distended with a greater ease (wild-type 0.03876 ml/cm $H_2O$, knockout 0.04564 ml/cm $H_2O$). Finally, because the PV loops (FIG. 4A) capture the quasi-static mechanical properties of the respiratory system, quasi-static compliance can be derived as the slope of the PV loop. Quasi-static compliance reflects the static elastic recoil pressure of the lungs at a given lung volume, which eliminates the effect of airway resistance. Like compliance, quasi-static compliance is increased in patients with emphysema[14], and in the mice, quasi-static compliance was significantly increased as well from 0.066 ml/cm $H_2O$ for the wild-types to 0.080 ml/cm $H_2O$ for the knockouts (FIG. 4C). In summary, the pulmonary mechanics phenotype observed in the knockout mice is very comparable to that of patients with emphysema. Besides pulmonary mechanics, morphometry can also be evaluated, i.e. the lung architecture and structure can quantitatively be characterized. AAT patients present with panacinar emphysema, i.e. alveoli and alveolar ducts are uniformly enlarged[15]. Therefore, a subset of the mice (n=7 per group) was analyzed to assess their lung morphometry. Following pulmonary testing, the lungs were filled with a mixture of agarose and formalin in order to preserve their internal structure, lung volume was determined, and tissue sections were stained (FIG. 4D) prior to quantitative measurements. The total volume showed a trend towards the knockout group having on average a 22% higher volume (1.7 ml) than the wild-type group (1.4 ml, FIG. 4I). The mean linear intercept, i.e. the mean free distance in the acinar air space complex, was significantly increased by ~9% from 43.1 m for the wild-type to 47.05 μm for the knockouts (FIG. 4E). This measurement indicates that in the knockouts, the alveolar ducts and alveoli are enlarged, which recapitulates the clinical characteristics of emphysema.

Example 5. Spontaneous Emphysema in Untreated Serpina1 Knockouts

Figure 5A:
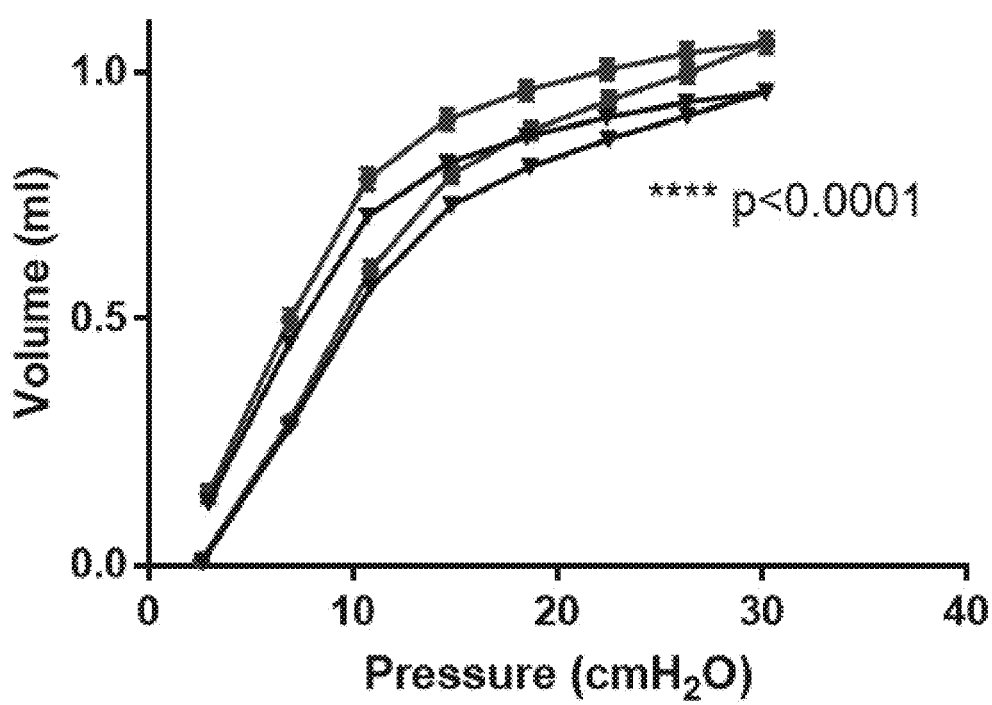
FIGS. 5A-F. Spontaneous emphysema in untreated Serpina1 knockouts. Pulmonary mechanics were assessed using a flexiVent in 35 weeks old (A-B) and 50 weeks old (C-D) wild-type mice (black triangles) and Serpina1 knockout mice (grey circles). Key parameters assessed include pressure-volume (PV) loop (A,C) and quasi-static compliance (B,D). Whole body plethysmography was performed on unrestrained, unanesthetized 50 week old wild-type mice (black triangles) and Serpina1 knockout mice (grey circles) (E-F). Key parameters assessed include expiratory time (E) and end expiratory pause (F). Statistical significance was determined by two-tailed unpaired t-test, except for the PV loops (2-way ANOVA).
Figure 5B:
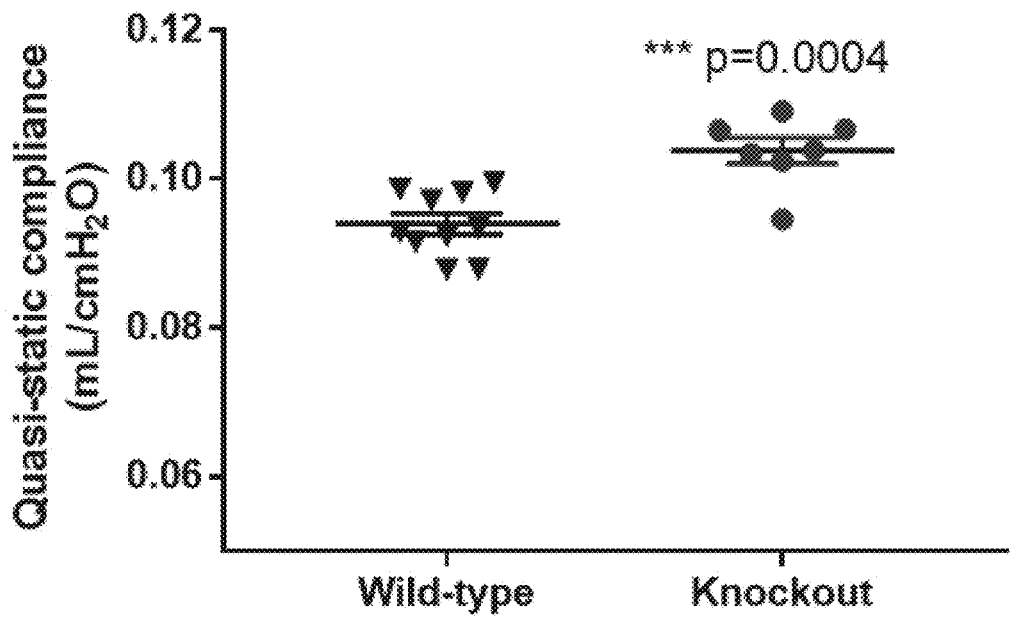
Figure 5C:
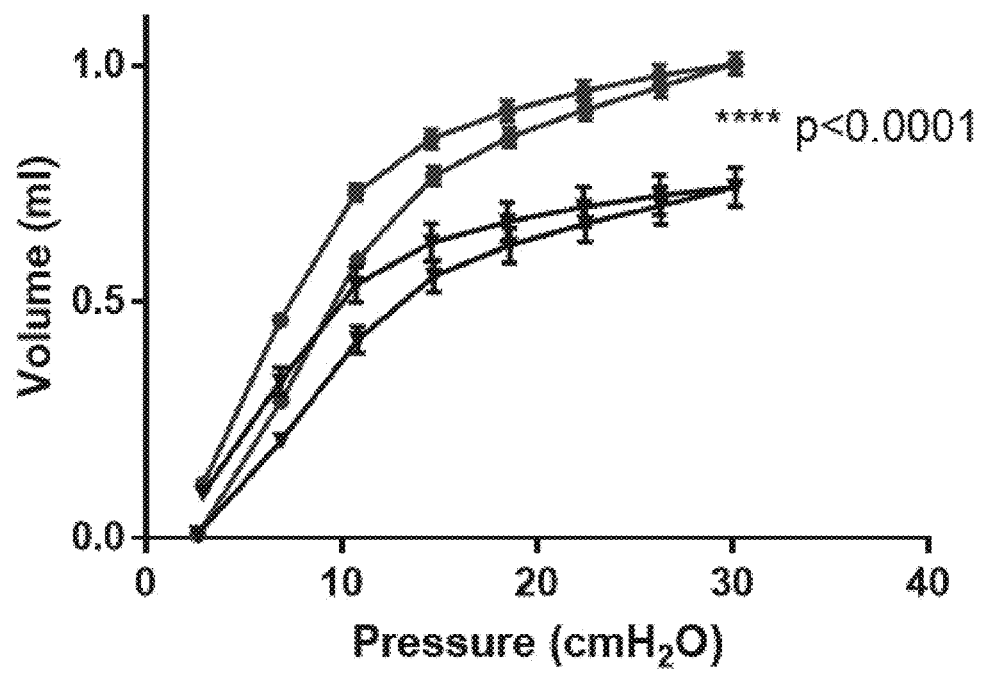
Figure 5D:
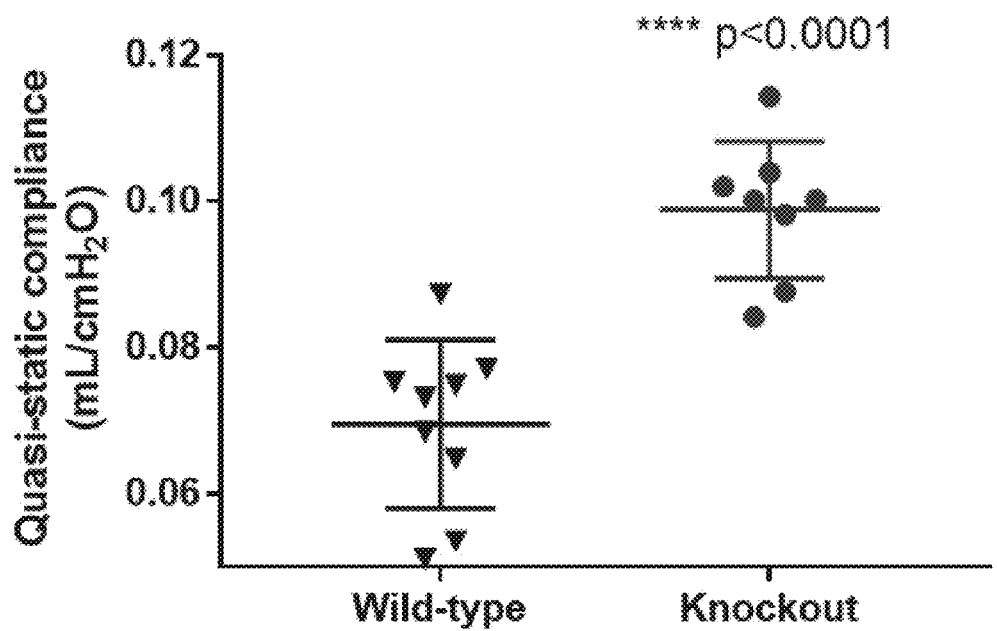

For the evaluation of the respiratory phenotype in response to aging, pulmonary mechanics were measured in age-matched, gender-matched wild-type and knockout mice at 35 and 50 weeks of age (FIGS. 5A-F). At 35 weeks of age, 7 knockout and 10 wild-type animals were analyzed. The PV loop of the knockouts is significantly different than that of the wild-types (FIG. 5A) and is shifted upwards indicating that a higher volume is displaced in response to pressure, which is characteristic of emphysema. Neither the dynamic elastance nor the dynamic compliance are affected (FIG. 6A-B). However, the quasi-static compliance is significantly increased in the knockouts (0.104 ml/cm $H_2O$) as compared to the wild-types (0.093 ml/cm $H_2O$, FIG. 5B). At 50 weeks of age, 9 knockout and 8 wild-type animals were analyzed. The PV loops are significantly different (FIG. 5C), and the difference between groups is larger at 50 weeks than at 35 weeks. Elastance is significantly reduced in the knockout group, with a value decreased from 24.53 cm $H_2O$/ml to 17.01 cm $H_2O$/ml (FIG. 6C, p=0.0002). Compliance is increased from 0.0417 ml/cm $H_2O$ in the wild-type group to 0.0591 ml/cm $H_2O$ in the knockout group (FIG. 6D, p<0.0001). The quasi-static compliance of the knockouts is also highly significantly increased from 0.0696 ml/cm $H_2O$ in the wild-types to 0.0989 ml/cm $H_2O$ in the knockouts (FIG. 5dD p<0.0001).

Figure 5E:
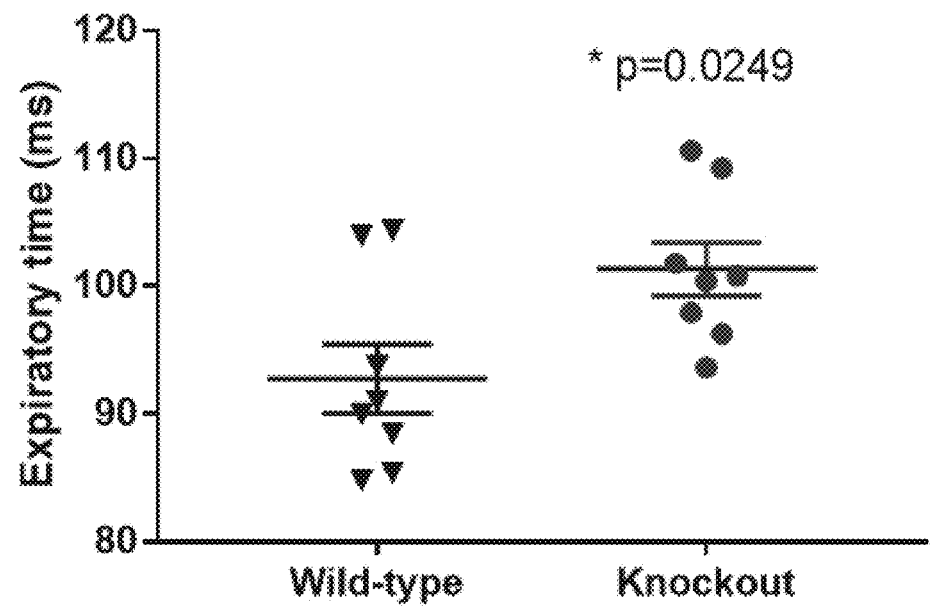
Figure 5F:
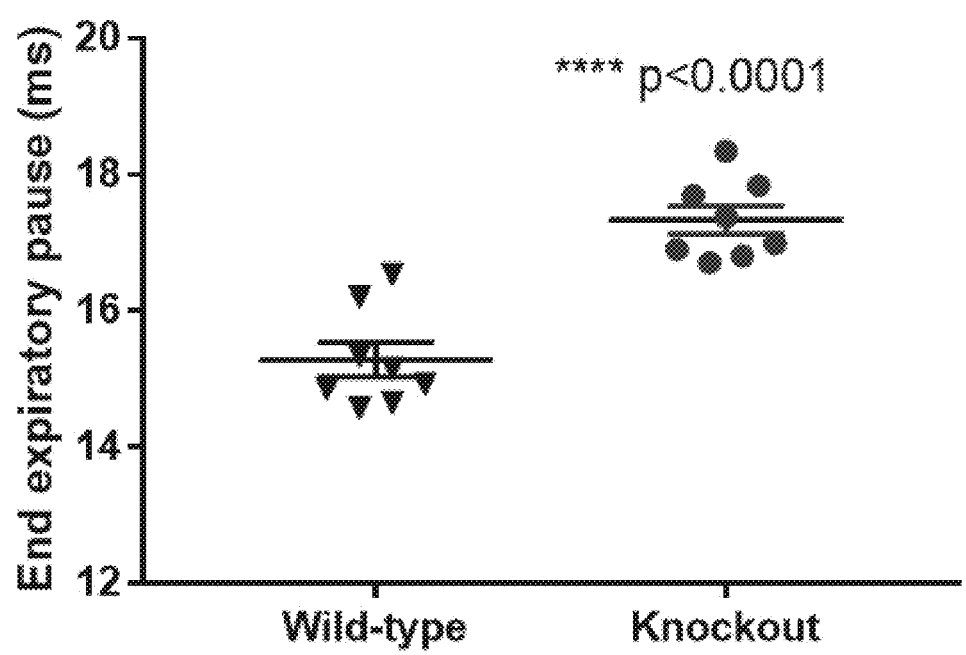

To further characterize the respiratory phenotype at 50 weeks of age, whole body plethysmography was performed in unrestrained, unanesthetized animals. In emphysema patients, the loss of elastic recoil—which is key to outward airflow—causes a decrease in expiratory flow and, in order to compensate, an increase in expiratory time to release the entire volume of gas. While inspiratory time of the knockout mice is unaffected during a hypercapnic challenge (FIG. 6E), expiratory time is increased (FIG. 5E, wild-type 92.74 ms, knockout 101.4 ms). End inspiratory pause (FIG. 6F, wild-type 1.764 ms, knockout 1.585 ms) and end expiratory pause (FIG. 5F, wild-type 15.28 ms, knockout 17.34 ms) are both significantly increased during hypercapnia. Finally, the enhanced pause (a controversial dimensionless parameter thought by some to be an indicator of airway hyper-responsiveness) is significantly increased during hypercapnia (FIG. 6G, wild-type 1.078, knockout 1.232).

Taken altogether, these results indicate that the knockout mice spontaneously develop emphysema, with early signs detectable at 35 weeks of age, and at 50 weeks of age they present with a clear emphysematous phenotype.

Figure 7:
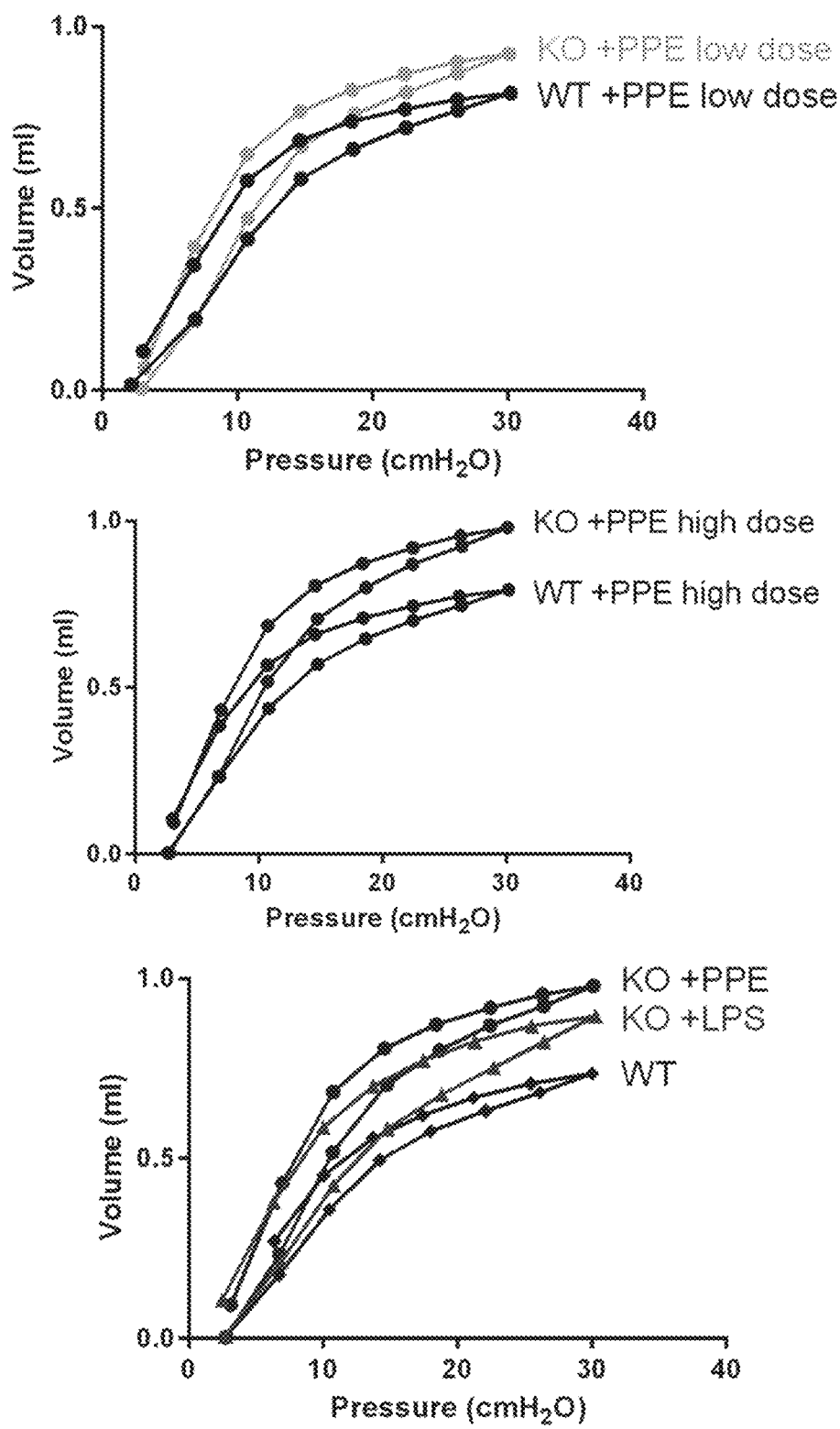
FIG. 7. Respiratory phenotype in response to a low and high dose of PPE.

When administering an intratracheal dose of 0.33 IU of porcine pancreatic elastase (PPE), a stronger phenotype is induced (FIG. 7).

REFERENCES

1 Buist, A. S. et al. International variation in the prevalence of COPD (the BOLD Study): a population-based prevalence study. Lancet 370, 741-750 (2007).
2 Lozano, R. et al. Global and regional mortality from 235 causes of death for 20 age groups in 1990 and 2010: a systematic analysis for the Global Burden of Disease Study 2010. Lancet 380, 2095-2128 (2012).
3 Lomas, D. A. & Silverman, E. K. The genetics of chronic obstructive pulmonary disease. Respir Res 2, 20-26 (2001).
4 Laurell, C. B. & Eriksson, S. The electrophoretic alpha1-globulin pattern of serum in alpha1-antitrypsin deficiency. 1963. COPD 10 Suppl 1, 3-8 (2013).
5 Flotte, T. R. et al. Phase 2 Clinical Trial of a Recombinant Adeno-Associated Viral Vector Expressing alpha(1)-Antitrypsin: Interim Results. Hum Gene Ther (2011).
6 Takubo, Y. et al. Alpha1-antitrypsin determines the pattern of emphysema and function in tobacco smoke-exposed mice: parallels with human disease. Am J Respir Crit Care Med 166, 1596-1603 (2002).
7 Barbour, K. W. et al. The murine alpha(1)-proteinase inhibitor gene family: polymorphism, chromosomal location, and structure. Genomics 80, 515-522 (2002).
8 Wang, D. et al. Deletion of Serpina1a, a murine alpha1-antitrypsin ortholog, results in embryonic lethality. Exp Lung Res 37, 291-300 (2011).
9 Paterson, T. & Moore, S. The expression and characterization of five recombinant murine alpha 1-protease inhibitor proteins. Biochem Biophys Res Commun 219, 64-69 (1996).
10 Yang, H., Wang, H. & Jaenisch, R. Generating genetically modified mice using CRISPR/Cas-mediated genome engineering. Nat Protoc 9, 1956-1968 (2014).
11 Bae, S., Park, J. & Kim, J. S. Cas-OFFinder: a fast and versatile algorithm that searches for potential off-target sites of Cas9 RNA-guided endonucleases. Bioinformatics 30, 1473-1475 (2014).
12 Cradick, T. J., Qiu, P., Lee, C. M., Fine, E. J. & Bao, G. COSMID: A Web-based Tool for Identifying and Validating CRISPR/Cas Off-target Sites. Mol Ther Nucleic Acids 3, e214 (2014).
13 Grinnan, D. C. & Truwit, J. D. Clinical review: respiratory mechanics in spontaneous and assisted ventilation. Crit Care 9, 472-484 (2005).
14 Papandrinopoulou, D., Tzouda, V. & Tsoukalas, G. Lung compliance and chronic obstructive pulmonary disease. Pulm Med 2012, 542769 (2012).
15 Takahashi, M. et al. Imaging of pulmonary emphysema: a pictorial review. Int J Chron Obstruct Pulmon Dis 3, 193-204 (2008).
16 Mayer, A. S. et al. Occupational exposure risks in individuals with PI*Z alpha(1)-antitrypsin deficiency. Am J Respir Crit Care Med 162, 553-558 (2000).
17 Piitulainen, E., Tornling, G. & Eriksson, S. Effect of age and occupational exposure to airway irritants on lung function in non-smoking individuals with alpha 1-antitrypsin deficiency (PiZZ). Thorax 52, 244-248 (1997).
18 Senn, O., Russi, E. W., Imboden, M. & Probst-Hensch, N. M. alpha1-Antitrypsin deficiency and lung disease: risk modification by occupational and environmental inhalants. Eur Respir J 26, 909-917 (2005).
19 Lomask, M. Further exploration of the Penh parameter. Exp Toxicol Pathol 57 Suppl 2, 13-20 (2006).
20 Mitzner, W. & Tankersley, C. Interpreting Penh in mice. Journal of applied physiology 94, 828-831; author reply 831-822 (2003).
21 Martorana, P. A. et al. The pallid mouse. A model of genetic alpha 1-antitrypsin deficiency. Lab Invest 68, 233-241 (1993).
22 Wang, M. et al. PacBio-LITS: a large-insert targeted sequencing method for characterization of human disease-associated chromosomal structural variations. BMC Genomics 16, 214 (2015).
23 Drorbaugh, J. E. & Fenn, W. O. A barometric method for measuring ventilation in newborn infants. Pediatrics 16, 81-87 (1955).
24 ElMallah, M. K. et al. Retrograde gene delivery to hypoglossal motoneurons using adeno-associated virus serotype 9. Human gene therapy methods 23, 148-156 (2012).
25 Elmallah, M. K. et al. Sustained correction of motoneuron histopathology following intramuscular delivery of AAV in pompe mice. Mol Ther 22, 702-712 (2014).
26 ElMallah, M. K. et al. Stimulation of Respiratory Motor Output and Ventilation in a Murine Model of Pompe Disease by Ampakines. American journal of respiratory cell and molecular biology 53, 326-335 (2015).
27 McGovern, T. K., Robichaud, A., Fereydoonzad, L., Schuessler, T. F. & Martin, J. G. Evaluation of respiratory system mechanics in mice using the forced oscillation technique. J Vis Exp, e50172 (2013).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse whose genome comprises inactivating mutations in exon 2 of each of Serpina1a, Serpina1b, Serpina1c, Serpina1d, and Serpina1e genes, and which expresses no hepatic or circulatory Alpha-One Antitrypsin (AAT) protein.

2. The transgenic mouse of claim 1, wherein the inactivating mutations comprise deletions in exon 2.

3. The transgenic mouse of claim 1, which is a mouse model of Alpha-One Antitrypsin (AAT)-deficiency lung disease.

4. An isolated cell, tissue, or organ from the transgenic mouse of claim 1.

5. A method of identifying a candidate compound for the treatment of Alpha-One Antitrypsin (AAT)-deficiency lung disease, the method comprising:
   contacting the transgenic mouse of claim 1 or a cell, tissue, or organ from the lung or liver of the transgenic mouse of claim 1, with a test compound;
   measuring levels of elastase in the animal, cell, tissue, or organ in the presence and absence of the test compound; and
   identifying a test compound that increases levels of elastase as a candidate compound.

6. A method of identifying a candidate therapeutic compound for the treatment of Alpha-One Antitrypsin (AAT)-deficiency lung disease, the method comprising:
   exposing the transgenic mouse of claim 1, which is a mouse model of Alpha-One Antitrypsin (AAT)-deficiency lung disease, to a test compound;
   measuring one or more parameters of respiratory physiology in the mouse in the presence and absence of the test compound; and
   identifying a test compound that improves the one or more parameters as a candidate therapeutic compound.

7. The method of claim 6, wherein the one or more parameters of respiratory physiology is selected from the group consisting of respiratory volume, inspiratory capacity, elastance, compliance, and quasi-static compliance.

* * * * *